United States Patent [19]
Lin

[11] 3,983,116
[45] Sept. 28, 1976

[54] HERBICIDAL TRIAZINES

[75] Inventor: Kang Lin, Newark, Del.

[73] Assignee: E. I. Du Pont de Nemours and Company, Wilmington, Del.

[22] Filed: June 5, 1974

[21] Appl. No.: 476,553

Related U.S. Application Data

[63] Continuation-in-part of Ser. No. 348,321, April 5, 1973, abandoned, which is a continuation-in-part of Ser. No. 256,249, May 24, 1972, abandoned.

[52] U.S. Cl. .................. 260/249.5; 260/248 NS; 71/93
[51] Int. Cl.² ................................... C07D 251/46
[58] Field of Search ........................... 260/249.5

[56] References Cited
FOREIGN PATENTS OR APPLICATIONS

| | | |
|---|---|---|
| 2,254,200 | 5/1974 | Germany |
| 814,948 | 6/1959 | United Kingdom |

OTHER PUBLICATIONS

Schaefer et al., *J. Am. Chem. Soc.,* vol. 73, pp. 2996–2999 (1951).
Smolin et al., Chem. of Hetocyclic Compounds, "s—Triazines & Deriv.," Interscience Pub., (N.Y.) pp. 276–277 (1959).

Primary Examiner—John M. Ford

[57] ABSTRACT

Compounds of the formula:

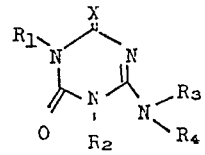

wherein X is oxygen or sulfur; $R_1$ is alkyl, alkenyl, alkynyl, cycloalkyl, cycloalkenyl, cycloalkylmethyl, cycloalkenylmethyl, bicycloalkyl, bicycloalkenyl, bicycloalkylmethyl, bicycloalkenylmethyl, phenyl, substituted alkyl, substituted cycloalkyl, or substituted phenyl; $R_2$ is hydrogen or alkyl; $R_3$ is H, methyl, or ethyl; and $R_4$ is alkyl, alkenyl, alkynyl, or methoxy; and the salts with bases of those compounds wherein $R_2$ is hydrogen, are useful as herbicides. A preferred compound is 1-methyl-3-cyclohexyl-6-dimethylamino-s-triazine-2,4(1H,3H)-dione.

11 Claims, No Drawings

HERBICIDAL TRIAZINES

CROSS-REFERENCE TO RELATED APPLICATIONS

This application is a continuation-in-part of application Ser. No. 348,321, filed Apr. 5, 1973, which is, in turn, a continuation-in-part of application Serial No 256,249, filed May 24, 1972. The entire disclosure of said application Ser. Nos. 348,321 and 256,249 is hereby incorporated by reference, both now abandoned.

BACKGROUND OF THE INVENTION

The invention relates to s-triazine herbicides, more particularly to a novel class of 6-amino-s-triazinediones and their use as herbicides.

Neumayer et al., "Pesticides", *Chemical Week*, Apr. 12 and 26, 1969, lists several commercial and experimental s-triazine herbicides. Among these are two well-known products, atrazine and simazine:

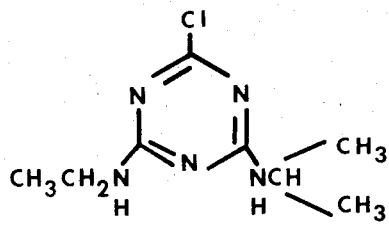

Atrazine

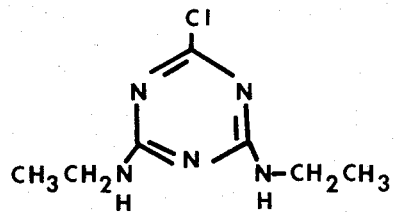

Simazine

Luckenbaugh U.S. Pat. Nos. 3,505,323 and 3,505,057 teach a class of tetrahydro-s-triazinediones of formula A below, and their use as herbicides. German Offenlegungsschrift No. 1,962,797 discloses a class of s-triazinones of formula B, below, and their use as herbicides.

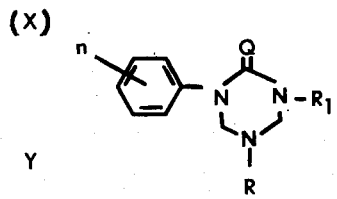

(A)

Q = S or O
X = halogen
Y = H, halogen, alkyl, etc.
R and $R_1$ = alkyl
n = 1 or 2

Chem. Ber. 104, 1606 (1971) relates to the preparation of s-triazinethiones by cyclocondensation of ethoxycarbonyl isothiocyanate with amidines, isoureas, isothioureas, and guanidines:

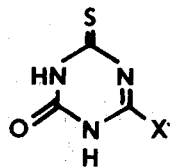

where X is, inter alia, $(C_2H_5)_2N-$, $(C_2H_5CH_2)_2N-$ or $(C_6H_5)_2N-$.

SUMMARY OF THE INVENTION

This invention relates to novel compounds of formula I and their use as herbicides

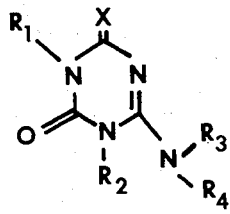

wherein
$R_1$ is selected from alkyl of 2 through 8 carbon atoms, alkenyl of 3 through 6 carbon atoms, alkynyl of 3 through 6 carbon atoms, cycloalkyl of 4 through 8 carbon atoms, cycloalkenyl of 5 through 8 carbon atoms, cycloalkylmethyl of 4 through 9 carbon atoms, cycloalkenylmethyl of 6 through 9 carbon atoms, bicycloalkyl or bicycloalkenyl of 7 through 10 carbon atoms, and bicycloalkylmethyl or bicycloalkenylmethyl of 8 through 11 carbon atoms, trimethylcyclohexyl, and tetramethylcyclohexyl; the above alkyl groups substituted with one methoxy, ethoxy, methylthio, or ethylthio group; the above cycloalkyl groups substituted with one alkyl of 2 through 4 carbon atoms, 1 through 2 methyl groups, 1 through 2 chlorines or bromines, one methoxy or one ethoxy group; and

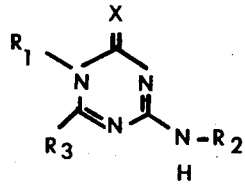

(B)

X = S or O
$R_1$, $R_2$, and $R_3$ = H or alkyl

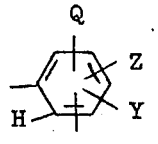

wherein
Q is hydrogen, fluorine, chlorine, bromine, alkyl of 1 through 4 carbon atoms, alkoxy or alkylthio of 1 through 2 carbon atoms, nitro or a trifluoromethyl group;

Y is hydrogen, chlorine, or methyl; and
Z is hydrogen or chlorine;
$R_2$ is hydrogen, alkyl of 1 through 3 carbon atoms or a cation selected from $Na^+$, $Li^+$, $K^+$, $(Ca/2)^+$, ammonium and dimethylammonium;
$R_3$ is hydrogen, methyl, or ethyl;
$R_4$ is alkyl of 1 through 4 carbon atoms, alkenyl of 3 through 4 carbon atoms, alkynyl of 3 through 4 carbon atoms, or methoxy; and
X is oxygen or sulfur;
provided that when X is sulfur, neither $R_2$ nor $R_3$ is hydrogen.

The invention also includes certain methods for making the above 6-aminotriazinediones, use of the 6-aminotriazinediones to control undesired vegetation, and herbicidal compositions containing the 6-aminotriazinediones.

Preferred are:
a. those compounds of formula I where:
$R_1$ is alkyl of 3 through 6 carbon atoms, cycloalkyl of 5 through 8 carbon atoms, or cycloalkyl of 5 through 8 carbon atoms substituted with one methyl group;
$R_2$, $R_3$, and $R_4$ are methyl; and
X is oxygen or sulfur;

b. those compounds of formula I where:
$R_1$ is alkyl of 3 through 6 carbon atoms; cycloalkyl of 5 through 8 carbon atoms; cyclopentyl substituted with one methyl group; cyclohexyl substituted with 1 or 2 methyl groups; 3-trifluoromethylphenyl; cyclohexenyl; or decahydronaphthen-1-yl;
$R_2$ and $R_3$ are methyl;
$R_4$ is hydrogen; and
X is oxygen; and c. those compounds of formula I where:
$R_1$ is cyclohexyl substituted with two methyl groups; 3-trifluoromethylphenyl; cyclohexenyl; decahydronaphthen-1-yl; or

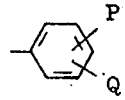

where P is hydrogen, methyl, chlorine, or fluorine; and Q is hydrogen or chlorine; $R_2$, $R_3$, and $R_4$ are methyl; and X is oxygen;

Especially preferred are:
a. preferred compounds (a) above;
b. those of preferred compounds (b) above wherein:
$R_1$ is alkyl of 3 through 4 carbon atoms; neopentyl; 1-ethylpropyl; n-hexyl; cycloalkyl of 5 through 8 carbon atoms; 2-methylcyclohexyl; 3-methylcyclohexyl; 2,3-dimethylcyclohexyl; 3,4-dimethylcyclohexyl; 2,4-dimethylcyclohexyl; 2,6-dimethylcyclohexyl; 3,5-dimethylcyclohexyl; 3-trifluoromethylphenyl; 3-cyclohexen-1-yl; or 1-decahydronaphthyl; and c. those of preferred compounds (c) above wherein:
$R_1$ is 2,4-dimethylcyclohexyl; 2,6-dimethylcyclohexyl; 2,3-dimethylcyclohexyl; 3,4-dimethylcyclohexyl; 3-trifluoromethylphenyl; 3-cyclohexen-1-yl; 1-decahydronaphthyl; phenyl; 3-methylphenyl; 4-methylphenyl; 3,4-dichlorophenyl; 2,5-dichlorophenyl; 2-chlorophenyl; 3-chlorophenyl; 4-chlorophenyl; 2-fluorophenyl; 3-fluorophenyl; 2-methyl-5-chlorophenyl; or 3-chloro-4-methylphenyl.

More preferred are those compounds of formula I where $R_1$ is cyclopentyl, methylcyclopentyl, cyclohexyl, or methylcyclohexyl; $R_2$, $R_3$, and $R_4$ are methyl; and X is oxygen.

Most preferred are the following two compounds:
3-cyclohexyl-1-methyl-6-dimethylamino-s-triazine-2,4(1H,3H)-dione, and
3-cyclopentyl-1-methyl-6-dimethylamino-s-triazine-2,4 (1H,3H)-dione.

DESCRIPTION OF THE INVENTION

Synthesis of the Compounds

The compounds of formula I are made by the processes described and exemplified hereinafter:

The first method to be described starts with cyanamide and involves reaction steps 1 through 5 shown below.

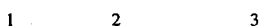

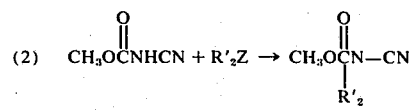

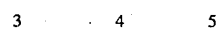

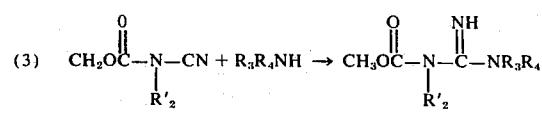

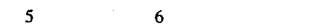

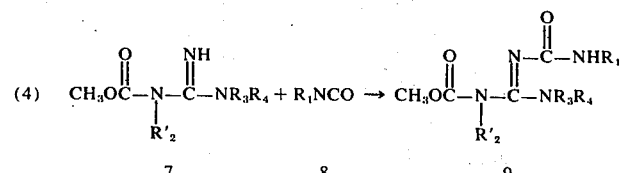

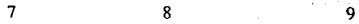

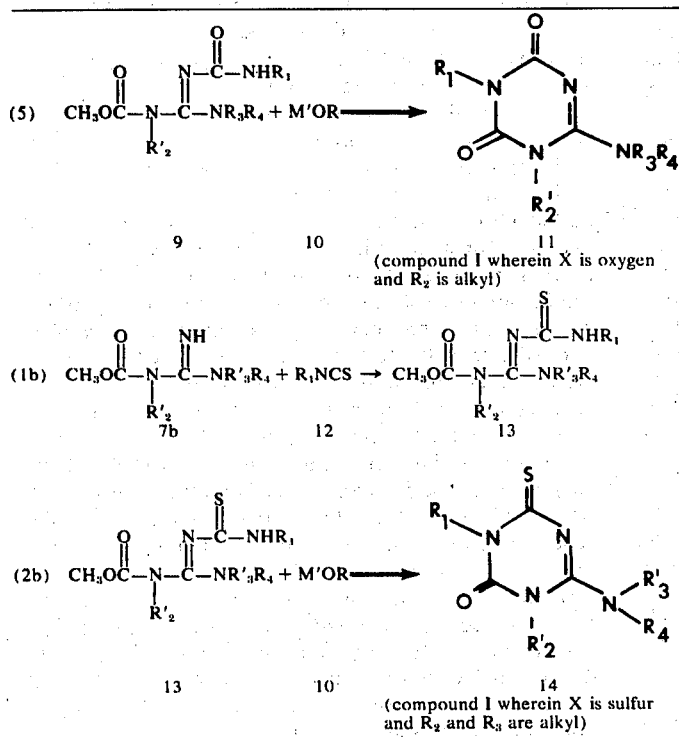

wherein: $R_1$, $R_3$ and $R_4$ are as previously defined, R is hydrogen or alkyl of 1 through 4 carbon atoms, $R'_2$ is that part of $R_2$ limited to alkyl, $R'_3$ is that part of $R_3$ limited to alkyl, M' is alkali metal, and Z is iodide or

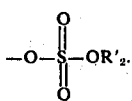

The process of preparation of methyl cyanocarbamate (compound 3) from cyanamide (compound 1) and methyl chloroformate (compound 2) is described in U.S. Pat. No. 3,657,443 (Equation 1).

An aqueous solution of the sodium salt of compound 3, containing from 15 to 35% of 3, preferably 20 to 30%, is reacted at 10° to 70°C., preferably 25° to 45°C., with 0.9 to 1.4, preferably 1.0 to 1.2, molecular equivalents of an alkylating agent 4 (for example, dimethyl sulfate) during a period of 2 to 16 hours, preferably 4 to 8 hours (Equation 2). As the reaction proceeds a second phase of compound 5 forms. After the reaction has proceeded for the desired time the upper layer of compound 5, which contains some water, is separated and the lower aqueous layer is contacted with an organic solvent selected from methylene chloride, dichloroethane, triclene, benzene, toluene and xylene; toluene is preferred. Other dialkyl sulfates (or alkyl halides) can be used instead of dimethyl sulfate, the sulfates being preferred for economic reasons.

The extract and the upper layer are analyzed for compound 5 by gas chromatography and added to an aqueous solution containing 15 to 75%, preferably 25 to 50% of the hydrochloride or sulfate of compound 6, preferably the sulfate (Equation 3). The mole ratio of amine salt to compound 5 can be from 1 to 3, preferably 1.5 to 2.5. The extraction solvent used (e.g. toluene) is removed by either azeotropic or simple distillation, depending on the boiling point. The residual aqueous mixture is then agitated for from 3 to 10 hours at 50° to 110°C., preferably 85° to 95°C. (Equation 3). Higher temperatures require shorter reaction times and vice versa.

The resulting reaction mass contains compound 7 and byproduct trisubstituted guanidine as well as unreacted compound 6, all present as salts. Before proceeding with the reaction of compound 7 with compound 8 it is necessary to liberate the free bases and remove the excess compound 6 to prevent the formation of by-product ureas. This operation can be effected by adding 50% aqueous sodium hydroxide equivalent to the amount of compounds 6 and 7 present, as determined by gas chromatographic analyses, and extracting with an organic solvent such as methylene chloride, followed by distilling a portion of the organic solvent to remove excess compound 6, or by removing compound 6 directly from the aqueous solution by distillation or by stripping with an inert gas after first adding base to form the free amine. The latter procedure is preferred. Compound 7 is relatively unstable in aqueous solution when present as the free base and tends to decompose into the corresponding trisubstituted guanidine. The rate of decomposition is directly proportional to pH and temperature. Therefore, when removing excess compound 6 by direct distillation or stripping from water it is advantageous to use a vacuum and to perform the operation as rapidly as possible.

The above described aqueous distillation procedure can be operated batchwise or continuously. It is preferred to carry out the operation in a continuous manner so that the exposure of compound 7 to high temperature and high pH is reduced to a minimum. This is accomplished by adding aqueous alkali metal hydroxide to the product from reaction 3 in a pipe-line reactor or by running the product and the alkali metal hydroxide into a small agitated vessel with a short holdup time, from 0 to 10 minutes, preferably 0 to 2 minutes. If the concentration of amine salt used is such that sodium salt precipitates during this neutralization additional water must be added to maintain this salt in solution.

The overflow from this vessel is fed to a distallation column operated under vacuum. The column is heated by feeding steam into the bottom; compound 6 and water are taken off as distillate (overhead) and an aqueous solution of compound 7 and trisubstituted guanidine as bottoms.

The condition under which the column can be operated are numerous and depend to some extent on the nature of compound 6. However, in general, conditions are selected so that the temperature of the feed to the column is not over 50°C. This necessitates cooling the product from equation 3 to approximately 30°C. before adding the caustic. The column is operated at a pressure of 25 to 300 mm of Hg preferably 50 to 150 mm and the amount of steam fed to the bottom of the column is adjusted such that the amount of water taken overhead along with compound 6 is equivalent to 5 to 25% of the weight of the reaction mass from equation 3.

The bottoms from the above distillation are fed into a hold tank which is maintained at a pH of 5 to 7 by the continuous addition of either sulfuric or hydrochloric acid; sulfuric is preferred. The concentrate of compound 7 in the neutralized solution is maintained at 15 to 50%, preferably 20 to 40%. The concentration will depend upon the strength of the salt solution of compound 6, base and acid solutions employed in the previous steps, and the amount of concentration or dilution which occurred during the distillation. The temperature of this solution is maintained at 25° to 45°C., preferably 25° to 35°, by either cooling the bottoms in a continuous-type cooler before neutralization or by cooling the neutralization vessel itself.

Reaction 4 is performed by preparing a mixture of the above solution and a solvent such as benzene, chlorobenzene, toluene or xylene; toluene is preferred. The amount of solvent added should be sufficient to dissolve the amount of compound 9 which will be formed. Generally the amount of solvent used is about 7 to 10 times the amount of compound 7 present in the aqueous solution.

An amount of compound 8 which is stoichiometrically equivalent to 85 to 100%, preferably 92 to 98%, of the compound 7 present in the aqueous layer is now added and with good agitation the addition of 50% aqueous caustic is started while the temperature is maintained at −5° to 50°C., preferably 5 to 35°C. by external cooling. The caustic addition is made as rapidly as heat can be removed to maintain the desired temperature and is continued until an amount stoichiometrically equivalent to the amount of acid used in neutralizing compound 7 has been added. If a solid phase of a sodium salt is now present, sufficient water should be added to dissolve it. The reaction is allowed to continue after the caustic addition is complete until the pH of the aqueous solution is nearly constant. This requires an addition time of 1 to 3 hours. Alternately, compound 8 and the aqueous caustic can be added simultaneously while the pH of the reaction mass is maintained at 9 to 10, preferably 9.3 to 9.7, during 1 to 4 hours, preferably 2 to 3. The aqueous sodium hydroxide addition is then continued until the pH is nearly constant. The agitation is stopped and the layers allowed to separate. The lower aqueous layer is removed and the upper organic layer is evaporated at a pressure of 50 to 760 mm/Hg, preferably 100 to 300 mm/Hg, until a clear distillate is obtained (indicating that all water has been removed).

The residual solution or slurry containing compound 9 is cooled, if necessary, to 25°–45°C., while anhydrous amine 6 (for example, dimethylamine) is added, either as a gas, or a liquid. It is preferred to add the amine 6 at 25°–35°C., but higher or lower temperatures can be used depending on the solubility of amine 6 in the particular solvent. It is important to have at least 1.0 and, preferably, 1.0 to 2.5 moles of amine 6.

Next the ring closure catalyst (compound 10) is added (Equation 5). The catalyst is an alkali metal alkoxide (or hydroxide) and it may be added either as a dry solid or as a solution in the alkanol. Dry sodium methoxide or a solution of sodium methoxide in methanol is a preferred catalyst. The amount of catalyst needed is from 0.1 to 5.0 mole percent of compound 9. Higher concentrations are not desirable because side reactions begin to intervene. A preferred concentration of compound 10 is from 1.0 to 2.0 mole percent of compound 9. The temperature is not critical and the ring-closure reaction can proceed at temperatures from 0°C. to 120°C provided that amine 6 is kept within the reaction system. The reaction is normally exothermic and the solution may be cooled if a lower temperature is required to retain amine 6. It is critical that the amine 6 remain present until ring closure is about complete.

After the catalyst is added, the reaction mass is held for 0.1 to 2.0 hours to insure completion of the ring closure. The reaction is rapid and normally is about complete in less than 1.0 hour.

The amine 6, by-product methanol, and part of the solvent are then removed by distillation, either at atmospheric or reduced pressure. Water is then added and the remainder of the solvent is removed by azeotropic distillation. The overhead water may be discarded or returned to the system, whichever is desirable. The amount of water remaining in the residue is not critical and may range from 0.1 to 5 or more parts per part of compound 11, depending on how compound 11 is to be isolated. Isolation can be by crystallization followed by filtration or centrifugation, by spray-drying, by phase-separation to remove most of the water, or by other conventional methods.

Alternatively, compound 11 can be recovered without distillation of all the methanol, amine 6 and solvent. If a poor solvent for compound 11, such as hexane, is added to the reaction mixture, compound 11 will precipitate and can be recovered by conventional methods.

The following examples further illustrate this method for synthesis of compounds of this invention.

In the examples all parts are by weight and all temperatures in degrees centigrade unless otherwise indicated. Refractive indices recorded as $n_D^{25}$ are values at 25°C.

EXAMPLE 1

A. Synthesis of N-Methoxycarbonyl-N-methylcyanamide (Equations 1 and 2)

To a solution of 504 parts of a 50% aqueous cyanamide solution in 825 parts of water at 25° are added during a period of 90 minutes and at a pH of 6.9–7.1 simultaneously 572 parts of methyl chloroformate and 945 parts of a 50% aqueous sodium hydroxide solution. As the addition of the reactants progresses, the temperature of the reaction is allowed to rise to 53°–55° and is maintained within that range by cooling. When the addition is complete, the reaction mass is cooled to 25°, whereupon crystallization of the sodium salt of methoxycarbonylcyanamide occurs. Dimethyl sulfate 775 parts) is then added, and agitation of the reaction mass is continued while maintaining the pH at 7–7.1 by a dropwise addition of about 25 parts of a 50% aqueous sodium hydroxide solution. After 6.5 hours, the resulting two-phase solution is repeatedly extracted with methylene chloride and the extract is dried. One half of the methylene chloride extract is then evaporated under vacuum, and the residue is distilled at 50°/0.5 mm. There is obtained 237.6 parts of N-methoxycarbonyl-N-methylcyanamide (69.5% yield).

By using the appropriate amount of diethyl sulfate, dipropyl sulfate or diisopropyl sulfate the following intermediate cyanamides can be prepared in a similar manner.

N-methoxycarbonyl-N-ethylcyanamide
N-methoxycarbonyl-N-propylcyanamide
N-methoxycarbonyl-N-isopropylcyanamide

B. Synthesis of N-methoxycarbonyl-N,N′,N′-trimethylguanidine (Equation 3)

A solution of 339 parts of dimethylamine hydrochloride in 500 parts of water is heated to 50°, and the remaining half of the above methylene chloride extract is added to it gradually, while at the same time the methylene chloride is removed by distillation. The resulting two-phase mixture is then heated for approximately 20 hours at 80°, after which time the starting N-methoxycarbonyl-N-methylcyanamide has nearly completely disappeared. The solution is then cooled to 0°, and 336 parts of a 50% aqueous sodium hydroxide solution is added. Repeated extraction of the reaction solution with methylene chloride and evaporation of the methylene chloride under vacuum gives 228.6 parts of crude N-methoxycarbonyl-N,N′,N′-trimethylguanidine of 84.4% purity, from which the pure product is isolated by distillation at 72°/0.5 mm.

By the above procedure using equivalent molecular weight amounts of the appropriate amines and appropriate N-methoxycarbamoyl-N′-alkylcyanamides the following intermediate guanidines can be prepared.

TABLE I

N-methoxycarbonyl-N-methyl-N′-ethyl-N′-methylguanidine
N-methoxycarbonyl-N-methyl-N′-isopropyl-N′-methylguanidine
N-methoxycarbonyl-N-methyl-N′-butyl-N′-methylguanidine
N-methoxycarbonyl-N-methyl-N′-allyl-N′-methylguanidine
N-methoxycarbonyl-N-methyl-N′-propargyl-N′-methylguanidine
N-methoxycarbonyl-N-methyl-N′-methoxy-N′-methylguanidine
N-methoxycarbonyl-N-ethyl-N′,N′-dimethylguanidine
N-methoxycarbonyl-N-isopropyl-N′,N′-dimethylguanidine
N-methoxycarbonyl-N-n-propyl-N′,N′-dimethylguanidine

C. Synthesis of Methyl N-(N-cyclohexylcarbamoyl-N′,N′-dimethylamidino)-N-methylcarbamate (Equation 4)

To 14.8 parts of the above crude N-methoxycarbonyl-N,N′,N′-trimethylguanidine in 50 parts of methylene chloride is added 11.0 parts of cyclohexyl isocyanate. The solution temperature reaches the boiling point, and when the temperature has fallen to 25°, the solvent is evaporated under vacuum to give an oil, which crystallizes when triturated with ether. Recrystallization from a mixture of carbon tetrachloride and petroleum ether gives pure methyl N-(N-cyclohexylcarbamoyl-N′,N′-dimethylamidino)-N-methylcarbamate, m.p. 93°–94°.

TABLE II

Following the general method of Example 1C, using the appropriate isocyanate as isothiocyanate as reactants with the appropriately substituted methoxycarbonylguanidine, the following compounds can be prepared.

Methyl N-(N-cyclopentylcarbamoyl-N′,N′-dimethylamidino)-N-methylcarbamate
Methyl N-[N-(2-methylcyclohexylcarbamoyl)-N′,N′-dimethylamino]-N-methylcarbamate
Methyl N-[N-(3-methylcyclohexylcarbamoyl)-N′,N′-dimethylamidino]-N-methylcarbamate
Methyl N-(N-cycloheptylcarbamoyl]-N′,N′-dimethylamidino)-N-methylcarbamate
Methyl N-(N-cyclooctylcarbamoyl-N′,N′-dimethylamidino)N-methylcarbamate
Methyl N-(N-cyclohexylcarbamoyl-N′,N′-dimethylamidino)-N-ethylcarbamate
Methyl N-(N-cyclohexylcarbamoyl-N′,N′-dimethylamidino)-N-n-propylcarbamate
Methyl N-(N-cyclohexylcarbamoyl-N′,N′-dimethylamidino)-N-isopropylcarbamate
Methyl N-(N-cyclohexylcarbamoyl-N′-butyl-N′-methylamidino)-N-methylcarbamate
Methyl N-(N-cyclohexylcarbamoyl-N′-allyl-N′-methylamidino)-N-methylcarbamate
Methyl N-(N-cyclohexylcarbamoyl-N′-propargyl-N′-methylamidino)-N-methylcarbamate
Methyl N-(N-cyclohexylcarbamoyl-N′-methoxy-N′-methylamidino)-N-methylcarbamate
Methyl N-(N-cyclopentylthiocarbamoyl-N′,N′-dimethylamidino)-N-methylcarbamate
Methyl N-(N-cyclohexylthiocarbamoyl-N′,N′-dimethylamidino)-N-methylcarbamate, m.p. 122°–123°
Methyl N-[N-(p-fluorophenylthiocarbamoyl)-N′,N′-dimethylamidino] -N-methylcarbamate, m.p. 132°–133°
Methyl N-[N-(m-fluorophenylthiocarbamoyl)-N′,N′-dimethylamidino]-N-methylcarbamate
Methyl N-[N-(sec-butylthiocarbamoyl)-N′,N′-dimethylamidino]-N-methylcarbamate
Methyl N-(N-neopentylthiocarbamoyl-N′,N′-dimethylamidino)-N-methylcarbamate
Methyl N-N-norbornylthiocarbamoyl-N′,N′-dimethylamidino)-N-methylcarbamate

D. Synthesis of 1-Methyl-3-cyclohexyl-6-dimethylamino-s-triazine-2,4(1H,3H)-dione (Equations 2, 3, 4, 5)

A 10% stoichiometric excess of dimethyl sulfate (906 parts is added at 25° with agitation to 3050 parts of an aqueous solution containing 797 parts of the sodium salt of compound 3 which has been adjusted to pH 7 with 50% aqueous sodium hydroxide. The reaction is allowed to continue for 6 hours while the temperature is maintained at 25° by external cooling and at pH 7 by the addition of 50% aqueous sodium hydroxide as required. During the reaction a separate phase of compound 5 ($R'_2 = CH_3$) is formed.

When the reaction is about complete the agitation is stopped and the layers allowed to separate. The upper layer of compound 5 ($R'_2 = CH_3$) is removed and the lower aqueous layer extracted with 2000 parts of toluene. The upper layer and the extract are added to 3300 parts of an agitated solution containing 920 parts of dimethylammonium sulfate in a vessel equipped for solvent removal. The resulting mixture is heated to 90° and vacuum applied to remove the toluene by azeotropic distillation. The distillation requires one hour and the reaction is continued for an additional 5 hours at 90°. The reaction mass is then cooled to 30°.

The above solution (3440 parts) is analyzed for dimethylamine and compound 5 ($R'_2=CH_3$) by gas chromatography and found to contain 264 parts of dimethylamine and 625 parts of compound 7 ($R'_2=R_3=R_4=CH_3$). The solution is then fed into a stirred vessel along with 50% aqueous sodium hydroxide at a rate of 28.6 parts of solution and 6.04 parts of 50% aqueous sodium hydroxide per minute. (This amount of sodium hydroxide frees compounds 6 and 7 from their salts; $R'_2=R_3=R_4=CH_3$.) The residence time in this vessel is two minutes. The effluent from this vessel is fed into the top of a packed column operated at 100 mm/Hg absolute pressure with total take-off. Atmospheric-pressure steam is fed into the bottom of the column at a rate such that the volume of $H_2O$ distilled over is 5 parts/minute. The stripped solution that exits the bottom of the column (into a vessel containing 800 parts of water) is continuously neutralized to pH 6.5 with concentrated sulfuric acid and cooled to 30° by external cooling.

When the distillation is complete the vacuum is broken and 4700 parts of toluene and 470 parts of cyclohexyl isocyanate (approximately 90% of the theoretical amount) are added to the neutralized still bottoms and 50% aqueous sodium hydroxide equivalent to the amount of sulfuric acid used in neutralizing the still bottoms is added during one-half hour while the temperature is maintained at 30° by external cooling.

The reaction is allowed to continue for an additional 3 hours until the pH becomes nearly constant at 8.8. The temperature is adjusted to 34° and maintained for 10 minutes after which time the agitator is turned off and the layers allowed to separate. The lower aqueous layer is removed and the toluene layer is distilled at 100 mm of Hg until a clear distillate is obtained.

Dimethylamine (375 parts) is sparged into the residue while the temperature is maintained at 25° by external cooling. Then 15.9 parts of a 25% solution of sodium methoxide in methanol is added with good agitation. The reaction is slightly exothermic and the temperature increases during 15 minutes to 35°. The reaction is allowed to continue for an additional one-half hour. The solution is then concentrated at 100 mm of Hg until 4000 parts of toluene have been removed. Water (1900 parts) is added and distillation is continued until toluene removal is complete. Water taken overhead is returned to the still pot via a water separator.

The residue is cooled to 15° and stirred until precipiation of the product is complete. The solids are collected by filtration and dried to give 745 parts (45.3% based on compound 3) of compound 11 ($R_1$=cyclohexyl; $R_3$=$R_4$=$R'_2$=methyl), m.p. 97°–100.5°. The aqueous filtrate can be recycled to lessen loss of product 11.

An alternate isolation of compound 11 from the aqueous solution is as follows: The aqueous residue from the distillation is heated to 60°. This results in the formation of a two-phase system. The lower organic layer is separated from the upper aqueous layer. The organic phase amounts to 1070 parts and contains 762 parts of compound 11. The water phase contains 77 parts of compound 11 and can be recycled back to the still pot to obtain higher overall recoveries.

The following s-triazinediones are prepared by cyclization of the appropriate methyl N-(N-substituted carbamoyl or thiocarbamoyl-N',N'-dialkylamidino)-N-alkylcarbamate by the above procedure.

TABLE III

1-Methyl-3-cyclopentyl-6-dimethylamino-s-triazine-2,4(1H,3H)-dione, m.p. 126°–129°
1-Ethyl-3-cyclohexyl-6-dimethylamino-s-triazine-2,4(1H,3H)-dione
1-Isopropyl-3-cyclohexyl-6-dimethylamino-s-triazine-2,4(1H,3H)-dione
1-Methyl-3-cyclohexyl-6-(N-butyl-N-methylamino9-s-triazine-2,4(1H,3H)-dione
1-Methyl-3-cyclohexyl-6-(N-allyl-N-methylamino)-s-triazine-2,4(1H,3H)-dione
1-Methyl-3-cyclohexyl-6-(N-propargyl-N-methylamino)-s-triazine-2,4(1H,3H)-dione
1-Methyl-3-cyclohexyl-6-(N-methoxy-N-methylamino)-s-triazine-2,4(1H,3H)-dione
1-Methyl-3-cyclohexyl-6-dimethylamino-s-triazine-4-thio-2,4(1H,3H)-dione, m.p. 210°–212°
1-Methyl-3-(p-fluorophenyl)-6-dimethylamino-s-triazine-4-thio-2,4(1H,3H)-dione, m.p. 224°–226°
1-Methyl-3-(m-fluorophenyl)-6-dimethylamino-s-triazone-4-thio-2,4(1H,3H)-dione, m.p. 204°–206°
1-Methyl-3-(sec-butyl)-6-dimethylamino-s-triazine-4-thio-2,4(1H,3H)-dione
1-Methyl-3-neopentyl-6-dimethylamino-s-triazine-4-thio-2,4(1H,3H)-dione
1-Methyl-3-(2-norbornyl)-6-dimethylamino-s-triazine-4-thio-2,4(1H,3H)-dione E. Alternate Synthesis of Methyl N-(N-cyclohexylcarbamoyl-N',N'-dimethylamidino)-N-methylcarbamate (Equation 4)

A solution of the sulfate salt of 7 as prepared in Example 1D is mixed with 4700 parts of toluene, and 470 parts of cyclohexyl isocyanate is added during 2 hours while the pH is maintained at 9.5 by the continuous addition of 50% aqueous sodium hydroxide. The sodium hydroxide addition is contained for an additional 3 hours until the pH becomes about constant at 9.5. The temperature is maintained at 30° throughout the reaction. The reaction mixture is worked up as in Example 1D to give methyl N-(N-cyclohexylcarbamoyl-N',N'-dimethylamidino)-N-methylcarbamate in about the same yield.

Equations 1b and 2b describe how to make those compounds of this invention where X is sulfur.

Equation 1b: The methoxycarbonylguanidine derivative 7b reacts with an isothiocyanate (12) in an inert solvent (such as tetrahydrofuran) at about room temperature to 100° for about 1 to 12 hours to form the methoxycarbonylallophanimidate 13. This intermediate can be isolated by evaporation of the solvent and further purified, if desired by recrystallization; or the intermediate can be used directly, without isolation, in the next step (2b).

Equation 2b: The methoxycarbonylallophanimidate 13 in an inert solvent (such as toluene) is treated with an alkali metal alkoxide or hydroxide (such as the methoxide of hydroxide of sodium or potassium) and the mixture heated to effect cyclization of compound 13 to the triazine-4-thione 14. Compound 14 can be isolated by cooling the reaction mixture and filtering off precipitated 14. If desired, 14 can be further purified by recrystallization from an inert solvent (such as ethyl acetate).

EXAMPLE 2

Synthesis of 1-Methyl-3-cyclohexyl-6-dimethylamino-s-triazine-4-thio-2,4(1H,3H)-dione A mixture of 100 parts of N-methoxycarbonyl-N,N',N'-trimethylguanidine, as prepared in 1B, 89 parts of cyclohexyl isothiocyanate and 0.5 parts of dibutyltin dilaurate is heated for 8 hours at 70° in 1000 parts of toluene. The clear, yellow solution is then heated to reflux and 50 parts of toluene is distilled out. A 12.5-part aliquot of 0.5M sodium methoxide in methanol solution is added over a 30-minute period, allowing toluene to distil out of the reaction mixture. After the addition is complete, additional toluene is distilled out until 500 parts of toluene have been removed. The reaction mixture is cooled and the resulting pale yellow product, 1-methyl-3-cyclohexyl-6-dimethylamino-s-triazine-4-thio-2,4(1H,3H)-dione, crystallizes. Filtration and drying affords 113 parts of product, m.p. 210°–212°.

The intermediate methyl N-(N-cyclohexylthiocarbamyl-N',N'-dimethylamidino)-N-methylcarbamate can be isolated by removing the toluene at reduced pressure and crystallizing the crude solid from ethyl acetate giving the purified intermediate, m.p. 122°–123°.

In some cases it is not necessary to add the base (sodium methoxide) to effect cyclization, for example to the first two triazine-4-thiones listed below.

Similarly the following compounds can be prepared using the appropriate reagents.

TABLE IV

1-Methyl-3-ethyl-6-dimethylamino-s-triazine-4-thio-2,4-(1H,3H)-dione, m.p. 139°–140°

1-Methyl-3-(n-butyl)-6-dimethylamino-s-triazine-4-thio-2,4(1H,3H)-dione, m.p. 124°–126°

1-Methyl-3-phenyl-6-dimethylamino-s-triazine-4-thio-2,4-(1H,3H)-dione, m.p. 209°–211°

1-Methyl-3-(o-fluorophenyl)-6-dimethylamino-s-triazine-4-thio-2,4-(1H,3H)-dione, m.p. 220°–221°

1-Methyl-3-(m-fluorophenyl)-6-dimethylamino-s-triazine-4-thio-2,4(1H,3H)-dione, m.p. 204°–206°

1-Methyl-3-(p-fluorophenyl)-6-dimethylamino-s-triazine-4-thio-2,4(1H,3H)-dione, m.p. 224°–226°

1-Methyl-3-(2-methylcyclohexyl)-6-dimethylamino-s-triazine-4-thio-2,4(1H,3H)-dione 1-Methyl-3-(3-methylcyclohexyl)-6-dimethylamino-s-triazine-4-thio-2,4-(1H,3H)-dione 1-Methyl-3-cycloheptyl-6-dimethylamino-s-triazine-4-thio-2,4(1H,3H)-dione 1-Methyl-3-cyclooctyl-6-dimethylamino-s-triazine-4-thio-2,4-(1H,3H)-dione 1-Methyl-3cyclohexyl-6-(N-methyl-N-butylamino)-s-triazine-4-thio-2,4(1H,3H)-dione 1-Methyl-3-cyclohexyl-6-(N-methyl-N-allylamino)-s-triazine-4-thio-2,4-(1H,3H)-dione An alternative method for preparing the compounds of this invention starts with a 2-methyl-2-thiopseudourea salt such as the sulfate or hydrochloride. A schematic representation of this method is shown by equations 6 through 12.

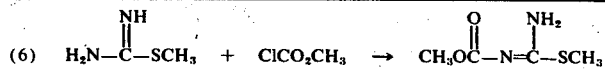

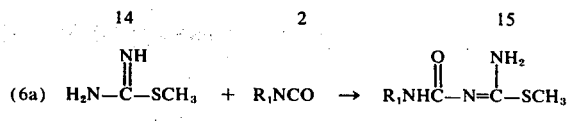

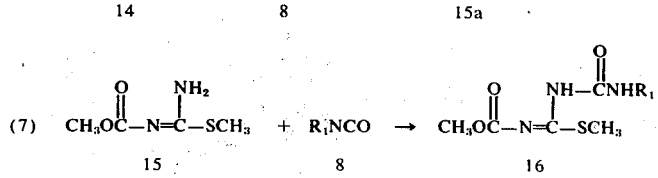

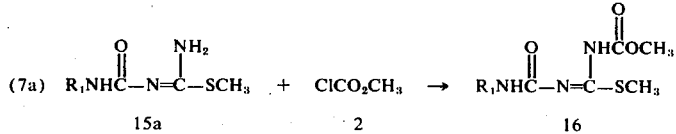

-continued
(8) 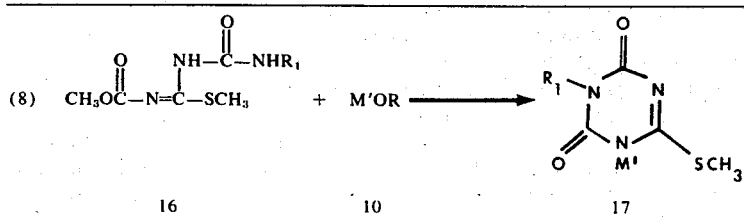
(9) 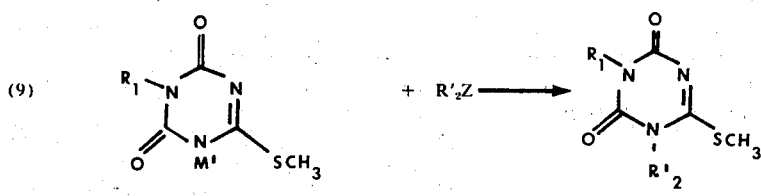
(10) 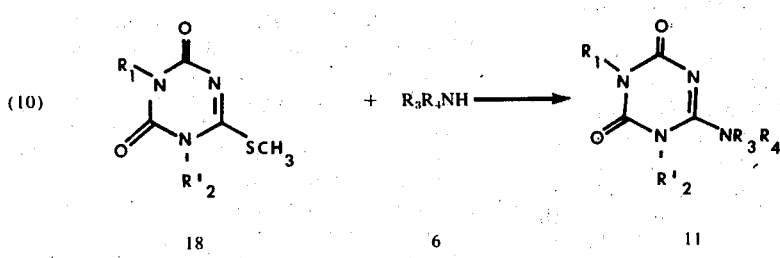
(11) 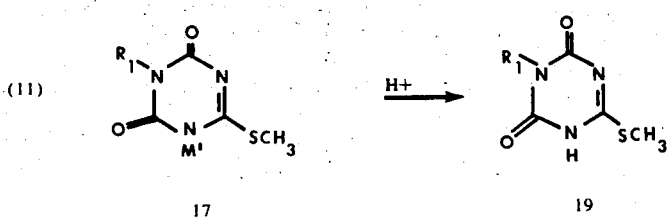
(12) 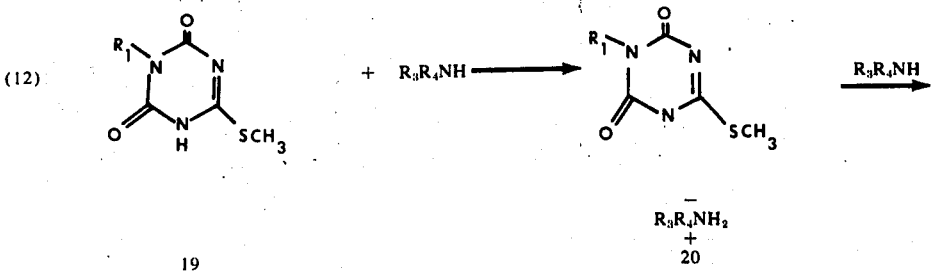
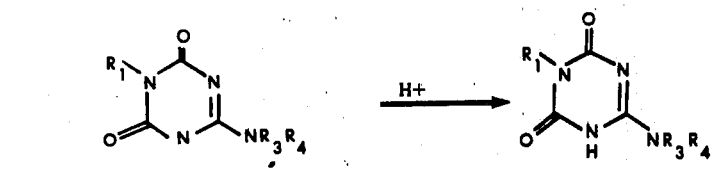

wherein: $R_1$, $R'_2$, $R_3$, $R_4$, R, M' and Z are as previously defined.

A suspension or solution of compound 14 is made in the selected solvent and treated with methyl chloroformate (Equation 6) or an isocyanate of formula $R_1NCO$ (Equation 6a) until the reaction is complete. The product, a 1-carbomethoxy-2-methyl-2-thiopseudourea (compound 15) or a 1-cyclohexyl-4-methyl-4-thiopseudobiuret (compound 15a) is treated with an isocyanate of formula $R_1NCO$ (Equation 7) or methyl chloroformate (Equation 7a) to give compound 16. A solution of compound 16 in a suitable solvent is treated with an alkali metal alkoxide to give the salt 17 (Equation 8). A solution or slurry of compound 17 in a selected solvent is reacted with an alkylating agent to give compound 18 (Equation 9). A suspension or solution of compound 18 in a selected solvent is treated with an amine (6) to give compound 11. The product, a s-triazine-2,4(1H,3H)-dione, can be isolated by conventional techniques as described above in the discussion of Equation 5.

In order to make those compounds of this invention where $R_2$ is hydrogen, the reactions of Equations 11 and 12 are carried out. Compound 17 is acidified with a mineral acid to compound 19 (Equation 11) which is then reacted in Equation 12 with an amine as described above for compound 18. The product formed is an amine salt 21 which can be used in the methods of this invention or can be acidified to give compound 22. Compound 22 will react with appropriate bases (such as ammonia, dimethylamine, and the hydroxides of lithium, sodium, potassium and calcium) to give the salts of this invention.

The solvents which can be used in these reactins are water, toluene, benzene, xylenes, monochlorobenzene, nitrobenzene, methylene chloride, triclene, perclene or mixtures of these organic solvents with water, i.e., the solvent need not be anhydrous.

With the above solvents it is practical to use a ratio of compound 14 to solvent such as 1:3 to 1:10, preferably from 1:3 to 1:6. Most preferred among this group of solvents in view of their lower cost and greater suitability for use in operation of this process are water, toluene, xylene and benzene.

The most preferred solvent for the conversion in Equation 6 is water. Mixtures of water and the organic solvents listed above can be used. With the above solvents it is practical to use a ratio of water:organic solvent of 1:1 to 1:6, most preferably 1:1 to 1:2.

The two-solvent system is most preferred for the reaction in Equation 6a, since the isocyanate 8 reacts with water to form undesired by-products.

Yield of product 15a from isocyanate could be seriously reduced by these side reactions.

The ratios of compounds 14:2 and 14:8 may be varied from 1:0.1 to 1:3, preferably from 1:0.8 to 1:2, most preferably 1:1 to 1:1.3.

The reactions 6 and 6a can be carried out from −10°C. to 50°C. but preferably from 0° to 30°C. and most preferably from 0° to 25°C.

The pH in reaction 6, 6a and 7a can be varied preferably from 6.5 to 11 and most preferably from 7–8.5.

The order of addition of reagents methyl chloroformate and isocyanate $R_1NCO$ vs. addition of aqueous base can be varied. The method chloroformate or isocyanate can be added first, followed by the aqueous base. But preferred is the simultaneous addition of methyl chloroformate or isocyanate and the aqueous base. The base can be selected from Li, Na and K hydroxide. The strength of the base to be added can vary from 10–50% but the higher concentration of base is most preferred because of the lower reaction volume for a given amount of product.

This simultaneous addition of metyl chloroformate or isocyanate $R_1NCO$ and 50% aqueous base gives a higher yield of product 15 or 15a because of the controlled pH conditions and shorter contact time with water required for completion of reaction.

The reactions 7 and 7a are preferably carried out between 0° and 50°C. and most preferably between 15° and 35°C.

The ratio of methyl chloroformate to 15a can be 1:1 to 4:1, preferably 1.5:1 to 3:1, most preferably 2:1 to 2.5:1. The ratio of isocyanate to 15 is preferably 1:1.1 to 1:1.5 and most preferably 1:1.05 to 1:1.15 in the interest of obtaining a high percentge conversion of compound 15 to compound 16 without the use of an unneeded excess of isocyanate or long reaction time.

The reaction time required for nearly complete reaction is preferably 0.5 to 12 hours for both Equations 6a and 7a and most preferably 1 to 4 hours. The reaction time is dependent on the nature and amount of solvent and reactants, temperature and type of mixing used.

The reaction time acquired for addition of methyl chloroformate or isocyanate is not critical and may vary from 0.1 to 10 hours, preferably from 0.1 to 4 hours and most preferably from 0.25 to 1.5 hours.

The compound 16 is preferably treated with 0.6 to 1.3 equivalents of alkali metal alkoxide and most preferably with 0.9 to 1.1 equivalents. The alkoxide can be used as the pure base or preferably as a solution in a suitable solvent and most preferably as a 15 to 35% solution in the corresponding alcohol.

The solution of compound 16 can be cyclized to compound 17 by use of an alkali metal hydroxide but an alcohol solvent must be added to dissolve the hydroxide before cyclization occurs.

The cyclization of compound 16 to compound 17 (Equation 8) takes place preferably at 25° to 70°C. but most preferably at 45° to 70°C.

The removal of solvent to give a slurry of compound 17 can be carried out under reduced pressure or at atmospheric pressure at a temperature of 20°C. to 135°C., but most preferably from 25° to 50°C. under reduced pressure and from 65° to 100°C. at atmospheric pressure.

The alkylation of compound 17 (Equation 9) with alkylating agent 4 (Z = halogen, alkylsulfate) can be carried out in a solvent such as water, toluene, benzene, xylene, chlorobenzene, nitrobenzene, acetonitrile, triclene or perclene.

The preferred solvent is water because of lower cost, simplicity of process operation and ease of isolation of the product 18. The product in this case can be isolated by filtration and drying or may be used directly as a wet solid in the next reaction by suspension in an organic solvent and removal of water by azeotropic distillation.

In the case where a dialkyl sulfate is used to alkylate compound 17, the pH of the aqueous solution or slurry should be maintained preferably between 7 and 11.5 and most preferably from 9–10.5 to avoid acidification of compound 17 to give compound 18 where $R'_2$ is H.

The ratio of alkylating agent to compound 17 is preferably 0.8 to 1 to 1.5 to 1 but most preferably 1.1 to 1.3:1. The reaction can be carried out at a temperature from 15° to 135°C if in an organic solvent and most preferably between 25° and 80°C.

When water is used as a solvent the preferred temperature range is 15°–80°C and the most preferred is 25°–40°C.

The conversion of the 6-methylthio-s-triazine-2,4(1H,3H)-dione (compound 18) to the 6-amino-s-triazine-2,4-(1H,3H)-dione 11 can be preferably carried out in a solvent selected from toluene, xylene, benzene, monochlorobenzene, triclene, perclene, nitrobenzene, methylene chloride and 1,2-dichloroethane. The most preferred solvent is toluene.

The preferred ratio of compound 18 to the amine is preferably 1:1 to 1:6 and most preferably, because of complete conversion to 11 and shorter reaction time required, 1:2 to 1:3. The amine in selected cases can be used as the solvent.

The conversion of compound 18 to compound 11 can be carried out at temperatures from 5° t0 135°C. but most preferably from 25 to 60°C.

The following examples illustrate the methods of Equations 6 through 12.

EXAMPLE 3

A. Synthesis of Methyl N-(1-amino-1-methylthiomethylene)-carbamate (Equation 6)

To a solution of 69.5 parts of 2-methyl-2-thiopseudourea sulfate and 47 parts of methyl chloroformate in 1000 parts of water at 0° is added dropwise, 56.9 parts of potassium hydroxide in 200 parts of water. The reaction mixture is stirred at room temperature for 3 hours and then extracted with methylene chloride. The methylene chloride extract is dried and the solvent evaporated on a rotary evaporator to give 45 parts of methyl N-(1-amino-1-methylthiomethylene)carbamate, m.p. 72°–77°.

B. Synthesis of Methyl 4-isopropyl-N-methoxycarbonyl-1-thioallophanimidate (Equation 7)

Seventy-four parts of methyl N-(1-amino-1-methylthiomethylene)carbamate and 47 parts of isopropyl isocyanate in 300 parts methylene chloride are stirred overnight. The solvent is evaporated on a rotary evaporator to give 113.6 parts of methyl 4-isopropyl-N-methoxycarbonyl-1-thioallophanimidate, m.p. 129°–132°.

Similarly are prepared the compounds in Table V.

TABLE V

Methyl 4-cyclopentyl-N-methoxycarbonyl-1-thioallophanimidate

Methyl 4-cyclohexyl-N-methoxycarbonyl-1-thioallophanimidate, m.p. 85–86

Methyl 4-(2-methylcyclohexyl)-N-methoxycarbonyl-1-thioallophanimidate

Methyl 4-(3-methylcyclohexyl)-N-methoxycarbonyl-1-thioallophanimidate,

Methyl 4-cycloheptyl-N-methoxycarbonyl-1-thioallophanimidate

Methyl 4-(3,5-dimethylcyclohexyl)-N-methoxycarbonyl-1-thioallophanimidate

Methyl 4-phenyl-N-methoxycarbonyl-1-thioallophanimidate

Methyl 4-(p-chlorophenyl)-N-methoxycarbonyl-1-thioallophanimidate, m.p. 127–128

Methyl 4-(3-chlorocyclobutyl)-N-methoxycarbonyl-1-thio-allophanimidate, m.p. 173–174.5

Methyl 4-(1-methylcyclopentyl)-N-methoxycarbonyl-1-thioallophanimidate

Methyl 4-(p-methylthiophenyl)-N-methoxycarbonyl-l-thioallophanimidate

Methyl 4-cyclohexylmethyl-N-methoxycarbonyl-1-thioallophanimidate, m.p. 132–134

Methyl 4-norbornyl-N-methoxycarbonyl-1-thioallophanimidate

C. Synthesis of 3-Isopropyl-6-methylthio-s-triazine-2,4(1H,3H)-dione (Equations 8 and 11)

One hundred parts of methyl 4-isopropyl-N-methoxycarbonyl-1-thioallophanimidate is refluxed for 1 hour with 27 parts of sodium methoxide in 200 parts methanol. The methanol is stripped on a rotary evaporator and the residue dissolved in 200 parts of water. The aqueous solution is neutralized with hydrochloric acid, the solid filtered off and dried to yield 55 parts of 3-isopropyl-6-methylthio-s-triazine-2,4(1H,3H)-dione, m.p. 188°–190°.

By the above method appropriate thioallophanimidates can be cyclized to the triazinediones illustrated below.

TABLE VI 3-(tert-butyl)-6-methylthio-s-triazinine-2,4(1H,3H)-dione 3-(sec-butyl)-6-methylthio-s-triazine-2,4-(1H,3H)-dione 3-cyclohexyl-6-methylthio-s-triazine-2,4(1H,3H)-dione, m.p. 255°–257°

3-cyclopentyl-6-methylthio-s-triazine-2,4(1H,3H)-dione, m.p. 201°–204°

3-(p-chlorophenyl)-6-methylthio-s-triazine-2,4(1H,3H)-dione, m.p. 292°–295°

3-(m-chlorophenyl)-6-methylthio-s-triazine-2,4(1H,3H)-dione, m.p. 192°–195.5°

3-(3,4-dimethylcyclohexyl)-6-methylthio-s-triazine-2,4(1H,3H)-dione 3-(4-tert-butylcyclohexyl)-6-methylthio-s-triazine-2,4(1H,3H)-dione 3-(2-methylcyclohexyl)-6-methylthio-s-triazine-2,4(1H,3H)-dione 3-(3-methylcyclohexyl)-6-methylthio-s-triazine-2,4-(1H,3H)-dione 3-cyclohepnyl-6-methylthio-s-triazine-2,4(1H,3H)-dione 3-phenyl-6-methylthio-s-triazine-2,4(1H,3H)-dione, m.p. 235°–245°

3-(3-chlorocyclobutyl)-6-methylthio-s-triazine-2,4(1H,3H)-dione, m.p. 167°–169°

3-(1-methylcyclopentyl)-6-methylthio-s-triazine-2,4(1H,3H)-dione, m.p. 192°–195.5°

3-cyclohexylmethyl-6-methylthio-s-triazine-2,4(1H,3H)-dione, m.p. 177.5°–178°

3-(2-norbornyl)-6-methylthio-s-triazine-2,4(1H,3H)dione

D. Synthesis of 1-Methyl-3-isopropyl-6-methylthio-s-triazine-2,4(1H,3H)-dione (Equation 9)

To a solution of 32 parts of sodium methoxide in 400 parts of methanol is added 132 parts of 3-isopropyl-6-methylthio-s-triazine-2,4(1H,3H)-dione. The solution is evaporated under vacuum, and the white solid is triturated with methylene chloride and filtered to give 110 parts of sodium 3-isopropyl-6-methylthio-s-triazine-2,4(1H,3H)-dione, m.p. above 300°.

Eighty parts of sodium 3-isopropyl-6-methylthio-s-triazine-2,4(1H,3H)-dione and 49 parts of methyl iodide are refluxed overnight in 700 parts of acetonitrile. The solvent is evaporated and the residue dissolved in methylene chloride. The methylene chloride solution is washed with water, dried, and evaporated to afford after recrystallization from 1-chlorobutane: hexane 54 parts of 1-methyl-3-isopropyl-6-methylthio-s-triazine-2,4(1H,3H)-dione, m.p. 74°–77°.

By the above procedure, using the appropriate 6-methylthio-s-triazinedione, a variety of compounds, illustrated below, can be prepared.

TABLE VII

1-Methyl-3-(3-chlorobutyl)-6-methylthio-s-triazine-2,4(1H,3H)-dione

1-Methyl-3-cyclopentyl-6-methylthio-s-triazine-2,4(1H,3H)-dione, m.p. 80°–83°

1-Methyl-3-cyclohexyl-6-methylthio-s-triazine-2,4(1H,3H)-dione, m.p. 135°–137°

1-Methyl-3-(2-methylcyclohexyl)-6-methylthio-s-triazine-2,4(1H,3H)-dione, m.p. 98°–100°

1-Methyl-3-(3-methylcyclohexyl)-6-methylthio-s-triazine-2,4(1H,3H)-dione, $n_D^{25}$ 1.5372

1-Methyl-3-cycloheptyl-6-methylthio-s-triazine-2,4(1H,3H)-dione, m.p. 98°–101°

1-Methyl-3-(1-methylcyclopentyl)-6-methylthio-s-triazine-2,4-(1H,3H)-dione, m.p. 84°–86°

1-Methyl-3-cyclohexylmethyl-6-methylthio-s-triazine-2,4(1H,3H)-dione, m.p. 102.5°–104°

1-Methyl-3-(2-norbornyl)-6-methylthio-s-triazine-2,4(1H,3H)-dione,

1-Methyl-3-phenyl-6-methylthio-s-triazine-2,4(1H,3H)-dione, m.p. 232.5°–233°

1-Methyl-3-(p-chlorophenyl)-6-methylthio-s-triazine-2,4(1H,3H)-dione, m.p. 146.5°–148.5°

1-Methyl-3-(m-chlorophenyl)-6-methylthio-s-triazine-2,4-(1H,3H)-dione, m.p. 297°–297.5°

1-Methyl-3-(tert-butyl)-6-methylthio-s-triazine-2,4(1H,3H)-dione,

1-Methyl-3-(sec-butyl)-6-methylthio-s-triazine-2,4(1H,3H)-dione,

1-Methyl-3-(3,5-dimethylcyclohexyl)-6-methylthio-s-triazine-2,4(1H,3H)-dione, $n_D^{25}$ 1.5400

1-Methyl-3-(tert-butylcyclohexyl)-6-methylthio-s-triazine-2,4(1H,3H)-dione

1-Methyl-3-(p-methylthiophenyl)-6-methylthio-s-triazine-2,4(1H,3H)-dione, m.p. 193°–195°

E. Synthesis of 3-Isopropyl-6-dimethylamino-s-triazine-2,4(1H,3H)-dione (Equation 12)

Ten parts of 3-isopropyl-6-methylthio-s-triazine-2,4(1H,3H)-dione, 10 parts of dimethylamine, and 50 parts of dioxane are heated in a bomb at 150° for 3 hours. The reaction is cooled and filtered to afford 5 parts of crude solid after filtration. The crude product is recrystallized from acetonitrile to give 2 parts of dimethylammonium 3-ispropyl-6-dimethylamino-s-triazine-2,4(1H,3H)-dione, m.p. 213°–215°.

To 2 parts of the above salt is added 10 parts of 1N hydrochloric acid. The solution is extracted with chloroform and the chloroform extract is dried and evaporated to afford 1 part of 3-isopropyl-6-dimethylamino-s-triazine-2,4-(1H,3H)-dione, m.p. 213°–214°.

F. Synthesis of Sodium 3-Isopropyl-6-dimethylamino-s-triazine 2,4(1H,3H)-dione To 6 parts of sodium methoxide in 60 parts of methanol is added 20 parts of 3-isopropyl-6-dimethylamino-s-triazine-2,4(1H,3H)-dione. The solution is stripped and the residue triturated with ether to afford after filtration 18 parts of sodium 3-isopropyl-6-dimethylamino-s-triazine-2,4(1H,3H)-dione, m.p. above 300°.

Using the above procedures the 6-alkylamino-s-triazines and their salts can be prepared. Some examples are as follows.

TABLE VIII 3-(tert-butyl)-6-methylamino-s-triazine-2,4(1H,3H)-dione 3-cyclohexyl-6-dimethylamino-s-triazine-2,4(1H,3H)-dione, m.p. 279° dec.

3-(tert-butyl)-6-dimethylamino-s-triazine-2,4(1H,3H)-dione, m.p. 206°–209°

3-sec-butyl)-6-methylamino-s-triazine-2,4(1H,3H)-dione, m.p. 161°–164°

3-(n-butyl)-6-methylamino-s-triazine-2,4(1H,3H)-dione 3-cyclohexyl-6-methylamino-s-triazine-2,4(1H,3H)-dione 3-(p-chlorophenyl)-6-dimethylamino-s-triazine-2,4(1H,3H)-dione, m.p. 265°–267°

3-(3-pentyl)-6-dimethylamino-s-triazine-2,4(1H,3H)-dione, m.p. 148°–151°

3-(3,4-dimethylcyclohexyl)-6-dimethylamino-s-triazine-2,4(1H,3H)-dione, m.p. 234°–237°

3-(4-tert-butylcyclohexyl)-6-dimethylamino-s-triazine-2,4-(1H,3H)-dione, m.p. 283°–285°

3-(2-methylcyclohexyl)-6-dimethylamino-s-triazine-2,4(1H,3H)-dione 3-(3-methylcyclohexyl)-6-dimethylamino-s-triazine-2,4(1H,3H)-dione 3-cycloheptyl-6-dimethylamino-s-triazine-2,4(1H,3H)-dione 3-phenyl-6-dimethylamino-s-triazine-2,4(1H,3H)-dione 3-(1-methylcyclopentyl)-6-dimethylamino-s-triazine-2,4(1H,3H)-dione 3-cyclohexylmethyl-6-dimethylamino-s-triazine-2,4(1H,3H)-dione 3-(2-norbornyl)-6-dimethylamino-s-triazine-2,4(1H,3H)-dione 3-isopropyl-6-dimethylamino-s-triazine-2,4(1H,3H)-dione, m.p. 213°–214°

3-isopropyl-6-dimethylamino-s-triazine dimethylamine salt, m.p. 213°–215°

3-isopropyl-6-dimethylamino-s-triazine lithium salt, m.p. >300°

3-isopropyl-6-methylamino-s-triazine ½ calcium salt, m.p. >300°

3-isopropyl-6-methylamino-s-triazine sodium salt, m.p. >300°

3-isopropyl-6-methylamino-s-triazine ammonium salt 3-isopropyl-6-methylamino-s-triazine potassium salt

G. Synthesis of 1-Methyl-3-isopropyl-6-dimethylamino-s-triazine-2,4(1H,3H)-dione (Equation 10)

A solution of 10 parts of 1-methyl-3-isopropyl-6-methylthio-s-triazine-2,4(1H,3H)-dione in 100 parts of tetrahydrofuran at 0° is saturated with dimethylamine. The reaction is allowed to warm to room temperature and stand overnight. The solvent is evaporated and the residue triturated with ether to afford 9 parts of 1-methyl-3-isopropyl-6-dimethylamino-s-triazine-2,4(1H,3H)-dione, m.p. 104°–106°.

EXAMPLE 4

Modified route for compounds with a bulky group is in the 3-position ($R_1$ in Formula I), using methyl chlorothiolformate 1-Methyl-3-(tert-butyl)-6-dimethylamino-s-triazine-2,4(1H,3H)-dione [Equations 6a, 7a(modified), 8,9,10]

To a solution of 278 parts of 2-methyl-2-thiopseudourea sulfate in 2000 parts of 50% aqueous methanol at 0° is added dropwise 176 parts of 50% sodium hydroxide, followed by 180 parts tert-butyl isocyanate in 400 parts tetrahydrofuran. The solution is partially evaporated on a rotary evaporator and the slurry filtered to yield, after drying, 180 parts of methyl 4-(tert-butyl)-1-thioallophanimidate, m.p. 102°–104°.

To a solution of 113.4 parts of the above compound and 80 parts of triethylamine in 1000 parts methylene chloride at 0° is added dropwise 66 parts methyl chlorothioformate in 100 parts of methylene chloride. The solution is stirred overnight, washed once with water, dried and evaporated to provide 76 parts methyl 4-(tert-butyl)-N-methylthiolcarbonyl-1-thioallophanimidate, m.p. 102°–105°.

Fifty parts of the above compound is refluxed for one hour with 30 parts of sodium methoxide in 500 parts of methanol. The reaction mixture is then cooled and the methanol is stripped on a rotary evaporator. The residue is washed with ether to provide 30 parts sodium 3-(tert-butyl)-6-methylthio-s-triazine-2,4(1H,3H)-dione.

Twenty-four parts of sodium 3-(tert-butyl)-6-methylthio-s-triazine-2,4(1H,3H)-dione and 15.5 parts of methyl iodide are refluxed overnight in 200 parts of acetonitrile. The solvent is evaporated and the residue dissolved in methylene chloride. The methylene chloride solution is washed with water, dried, and evaporated to afford, after recrystallization from 1-chlorobutane, 15 parts of 1-methyl-3-(tert-butyl)-6-methylthio-s-trizazine-2,4(1H,3H)-dione, m.p. 138°–140°.

A solution of 5 parts of the above material in 50 parts of tetrahydrofuran at 0° is saturated with dimethylamine. The reaction is allowed to warm to room temperature and stand overnight. The solvent is evaporated and the residue triturated with ether to afford 4 parts of 1-methyl-3-(tert-butyl)-6-dimethylamino-s-triazine-2,4(1H,3H)-dione, m.p. 161°–163°.

EXAMPLE 5

A. Preparation of 1-Methyl-3-cyclohexyl-6-methylthio-s-triazine-2,4(1H,3H)-dione (Equations 6, 7, 8, 9)

To a solution of 56 parts of 2-methyl-2-thiopseudourea sulfate in 300 parts of water at 0° are added dropwise simultaneously 37.5 parts of methyl chloroformate and 62 parts of 50% aqueous sodium hydroxide. The methyl chloroformate is added during 0.5 hr and the 50% aqueous sodium hydroxide as required to keep the pH of the reaction mass at 8.5. After the additions are complete, the reaction is brought to ambient temperature (25°–28°) and held there for 2 hours.

To this suspension of 1-carbomethoxy-2-methyl-2-thiopseudourea at 25°–28° is added 300 parts of toluene. Cyclohexyl isocyanate (44 parts) is added over 0.5 hr and then stirred at 25°–30° for an additional 2 hours. The toluene layer is then separated and 76 parts of a 25% sodium methoxide solution is added. The solution is then refluxed for 1 hour (65°–70°) and then a methanol-toluene mixture is distilled until a pot temperature of 88°–90° is attained.

This toluene slurry of 3-cyclohexyl-6-methylthio-s-triazine-2,4(1H,3H)-dione sodium salt is then agitated with 650 parts of water for 0.15 hrs. The aqueous layer is separated and reacted at 25°–30° during 0.25 hrs with 57 parts of dimethyl sulfate. After the dimethyl sulfate is added, the pH of the reaction is maintained at pH 9–9.5 by addition of a total of 7.5 parts of 50% aqueous sodium hydroxide. The total reaction time is 1.8 hrs at which time filtration and drying gives 70 parts of white 1-methyl-3-cyclohexyl-6-methylthio-s-triazine-2,4(1H,3H)-dione, m.p. 137°–139°.

B. Preparation of 1-Methyl-3-cyclohexyl-6-methylthio-s-triazine-2,4(1H,3H)-dione (Equations 6a, 7a, 8, 9)

To a solution of 70 parts of 2-methyl-2-thiopseudourea sulfate in 375 parts of water and 400 parts of toluene at 10° is added over 1 hour 62.5 parts of cyclohexyl isocyanate. The pH is maintained at 8.5 by addition of 80 parts of 50% aqueous sodium hydroxide over 1–1.5 hours. The two-phase system is then reacted with 99 parts of methyl chloroformate and 84 parts of 50% aqueous sodium hydroxide during 1 hour. The temperature is maintained at 25°–30°. After the addition is complete the reaction is stirred at 25°–28° for an additional 3 hours. The toluene layer is separated and treated as in Example 5A to give 76 parts of 1-methyl-3-cyclohexyl-6-methylthio-s-triazine-2,4-(1H,3H)-dione, m.p. 136°–138°.

C. Preparation of 1-Methyl-3-cyclohexyl-6-dimethylamino-s-triazine-2,4(1H,3H)-dione (Equation 10)

A suspension of 300 parts of 1-methyl-3-cyclohexyl-6-methylthio-s-triazine-2,4(1H,3H)-dione in 887 parts of toluene is stirred at 25°–30° for three hours with 150 parts of dimethylamine. Toluene is distilled from the reaction until a pot temperature of 125° is attained. The reaction mass is cooled to 50° at which time 480 parts of hexane is added over 0.66 hours. The slurry at 25° is filtered to give 282 parts of crystalline 1-methyl-3-cyclohexyl-6-dimethylamino-s-triazine-2,4(1H,3H)-dione, m.p. 110°–115°.

The following aminotriazinediones can be prepared by the procedures of Examples 3, 4 and 5 by using the appropriate reactants.

TABLE IX

1-Methyl-3-ethyl-6-dimethylamino-s-triazine-2,4(1H,3H)-dione, m.p. 104°–106°.
1-Methyl-3-propyl-6-dimethylamino-s-triazine-2,4(1H,3H)-dione, m.p. 106°–109°.
1-Methyl-3-isopropyl-6-dimethylamino-s-triazine-2,4(1H,3H)-dione, m.p. 104°–106°.
1-Methyl-3-isobutyl-6-dimethylamino-s-triazine-2,4(1H,3H)-dione, m.p. 87°–89°
1-Methyl-3-(2-cyclopenten-1-ylmethyl)-6-dimethylamino-s-triazine-2,4(1H,3H)-dione
1-Methyl-3-butyl-6-dimethylamino-s-triazine-2,4(1H,3H)-dione, m.p. 63°–65°
1-Methyl-3-sec-butyl-6-dimethylamino-s-triazine-2,4(1H,3H)-dione, m.p. $n_D^{25}$ 1.5198
1-Methyl-3-isobutyl-6-dimethylamino-s-triazine-2,4(1H,3H)-dione, m.p. 87°–89°.
1-Methyl-3-(tert-butyl)-6-dimethylamino-s-triazine-2,4(1H,3H)-dione, m.p. 161°–163°
1-Methyl-3-neopentyl-6-dimethylamino-s-triazine-2,4(1H,3H)-dione, m.p. 141°–144°
1-Methyl-3-hexyl-6-dimethylamino-s-triazine-2,4(1H,3H)-dione, $n_D^{25}$ 1.5130
1-Methyl-3-heptyl-6-dimethylamino-s-triazine-2,4(1H,3H)-dione,
1-Methyl-3-(2-ethylhexyl)-6-dimethylamino-s-triazine-2,4(1H,3H)-dione
1-Methyl-3-allyl-6-dimethylamino-s-triazine-2,4(1H,3H)-dione, m.p. 74°–75°
1-Methyl-3-(2-methallyl)-6-dimethylamino-s-triazine-2,4(1H,3H)-dione
1-Methyl-3-propargyl-6-dimethylamino-s-triazine-2,4(1H,3H)-dione
1-Methyl-3-(1-methylpropyn-2-yl)-6-dimethylamino-s-triazine-2,4(1H,3H)-dione
1-Methyl-3-(1-hexene-3-yl)-6-dimethylamino-s-triazine-2,4(1H,3H)-dione
1-Methyl-3-(2-hexenyl)-6-dimethylamino-s-triazine-2,4(1H,3H)-dione
1-Methyl-3-(1-hexyn-3-yl)-6-dimethylamino-s-triazine-2,4(1H,3H)-dione
1-Methyl-3-(3,4-dichlorophenyl)-6-dimethylamino-s-triazine-2,4(1H,3H)-dione, m.p. 211°–212°
1-Methyl-3-(2,5-dichlorophenyl)-6-dimethylamino-s-triazine-2,4(1H,3H)-dione, m.p. 191°–194°
1-Methyl-3-(p-chlorophenyl)-6-dimethylamino-s-triazine-2,4(1H,3H)-dione, m.p. 238°–239°
1-Methyl-3-(m-chlorophenyl)-6-dimethylamino-s-triazine-2,4(1H,3H)-dione, m.p. 141°–143°
1-Methyl-3-(o-chlorophenyl)-6-dimethylamino-s-triazine-2,4(1H,3H)-dione, m.p. 205°–207°
1-Methyl-3-(2-cycloocten-1-ylmethyl)-6-dimethylamino-s-triazine-2,4(1H,3H)-dione
1-Methyl-3-(m-fluorophenyl)-6-dimethylamino-s-triazine-2,4(1H,3H)-dione, m.p. 157°–159°
1-Methyl-3-(o-fluorophenyl)-6-dimethylamino-s-triazine-2,4(1H,3H)-dione, m.p. 179°–182°
1-Methyl-3-(p-fluorophenyl)-6-dimethylamino-s-triazine-2,4(1H,3H)-dione
1-Methyl-3-(3-chloro-4-fluorophenyl)-6-dimethylamino-s-triazine-2,4(1H,3H)-dione
1-Methyl-3-(chloro-6-methylphenyl)-6-dimethylamino-s-triazine-2,4(1H,3H)-dione, m.p. 155°–157°
1-Methyl-3-(3-chloro-4-methylphenyl)-6-dimethylamino-s-triazine-2,4(1H,3H)-dione, m.p. 189.5°–190.5°
1-Methyl-3-[m-(trifluoromethyl)phenyl]-6-dimethylamino-s-triazine-2,4(1H,3H)-dione, m.p. 144°–148°
1-Methyl-3-(m-nitrophenyl)-6-dimethylamino-s-triazine-2,4(1H,3H)-dione, m.p. 207°–209°
1-Methyl-3-phenyl-6-dimethylamino-s-triazine-2,4(1H,3H)-dione, m.p. 208°–210°
1-Methyl-3-(o-tolyl)-6-dimethylamino-s-triazine-2,4(1H,3H)-dione
1-Methyl-3-(m-tolyl)-6-dimethylamino-s-triazine-2,4(1H,3H)-dione, m.p. 159°–162°
1-Methyl-3-(3-(p-tolyl)-6-dimethylamino-s-triazine-2,4(1H,3H)-2,4(1H,3H)-dione, m.p. 237°–240°
1-Methyl-3-(3,4-xylyl)-6-dimethylamino-s-triazine-2,4(1H,3H)-dione
1-Methyl-3-(p-ethylphenyl)-6-dimethylamino-s-triazine-2,4(1P,3H)-dione
1-Methyl-3-(p-isopropylphenyl)-6-dimethylamino-s-triazine-2,4(1H,3H)-dione, m.p. 189°–191°
1-Methyl-3-(3-chloro-4-isopropylphenyl)-6-dimethylamino-s-triazine-2,4(1H,3H)-dione
1-Methyl-3-(p-bromophenyl)-6-dimethylamino-s-triazine-2,4(1H,3H)-dione
1-Methyl-3-[p-(tert-butyl)phenyl]-6-dimethylamino-s-triazine-2,4(1H,3H)-dione
1-Methyl-3-(p-methoxyphenyl)-6-dimethylamino-s-triazine-2,4(1H,3H)-dione
1-Methyl-3-(bicyclo[4.4.0]dec-2-ene-1-yl)-6-dimethylamino-s-triazine-2,4(1H,3H)-dione
1-Methyl-3-(bicyclo[4.4.0]dec-2-ene-1-ylmethyl)-6-dimethylamino-s-triazine-2,4(1H,3H)-dione
1-Methyl-3-(p-methylthiophenyl)-6-dimethylamino-s-triazine-2,4(1H,3H)-dione
1-Methyl-3-(p-ethoxyphenyl)-6-dimethylamino-s-triazone-2,4(1H,3H)-dione
1-Methyl-3-(3-chloro-4-nitrophenyl)-6-dimethylamino-s-triazine-2,4(1H,3H)-dione
1-Methyl-3-[4-chloro-3-(trifluoromethyl)phenyl]-6-dimethylamino-s-triazine-2,4(1H,3H)-dione
1-Methyl-3-(2,4,5-trichlorophenyl)-6-dimethylamino-s-triazine-2,4(1H,3H)-dione
1-Methyl-3-(3-methoxypropyl)-6-dimethylamino-s-triazine-2,4(1H,3H)-dione
1-Methyl-3-(3-ethoxypropyl)-6-dimethylamino-s-triazine-2,4(1H,3H)-dione
1-Methyl-3-(2-methoxyethyl)-6-dimethylamino-s-triazine-2,4(1H,3H)-dione
1-Methyl-3-(3-methylthiopropyl)-6-dimethylamino-s-triazine-2,4(1H,3H)-dione
1-Methyl-3-(2-ethylthioethyl)-6-dimethylamino-s-triazine-2,4(1H,3H)-dione
1-Methyl-3-(2-cyclopenten-1-yl)-6-dimethylamino-s-triazine-2,4(1H,3H)-dione
1-Methyl-3-(2-cyclohexen-1-yl)-6-dimethylamino-s-triazine-2,4(1H,3H)-dione
1-Methyl-3-(3-cyclohexen-1-yl)-6-dimethylamino-s-triazine-2,4(1H,3H)-dione
1-Methyl-3-(2-cycloocten-1-yl)-6-dimethylamino-s-triazine-2,4(1H,3H)-dione
1-Methyl-3-(5-norbornen-2-yl)-6-dimethylamino-s-triazine-2,4(1H,3H)-dione
1-Methyl-3-cyclopentylmethyl-6-dimethylamino-s-triazine-2,4(1H,3H)-dione
1-Methyl-3-cyclooctylmethyl-6-dimethylamino-s-triazine-2,4(1H,3H)-dione 1-Methyl-3-(3-cyclohexen-1-ylmethyl)-6-dimethylamino-s-triazine-2,4(1H,3H)-dione 1-Methyl-3-(2-norbornylmethyl)-6-dimethylamino-s-triazine-2,4(1H,3H)-dione 1-Methyl-3-(5-norboren-1-ylmethyl)-6-dimethylamino-s-triazine-2,4(1H,3H)-dione 1-Methyl-3-cyclobutyl-6-dimethylamino-s-triazine-2,4(1H,3H)-dione 1-Methyl-3-(1-methylcyclopentyl)-6-dimethylamino-s-triazine-2,4(1H,3H)-dione, m.p. 104°–106°

1-Methyl-3-cyclopentyl-6-dimethylamino-s-triazine-2,4(1H,3H)-dione, m.p. 126°–129°

1-Methyl-3-cyclohexyl-6-dimethylamino-s-triazine-2,4(1H,3H)-dione, m.p. 101.5°–104°

1-Methyl-3-(2-methylcylohexyl)-6-dimethylamino-s-triazine-2,4(1H,3H)-dione, m.p. 125°–126.5°

1-Methyl-3-(3-methylcyclohexyl)-6-dimethylamino-s-triazine-2,4(1H,3H)-dione, m.p. 91°–93°

1-Methyl-3-(1-methylcyclohexyl)-6-dimethylamino-s-triazine-2,4(1H,3H)-dione

1-Methyl-3-(4-methylcyclohexyl)-6-dimethylamino-s-triazine-2,4(1H,3H)-dione

1-Methyl-3-(2,4-dimethylcyclohexyl)-6-dimethylamino-s-triazine-2,4-(1H,3H)-dione, m.p. 120°–122°

1-Methyl-3-(3,4-dimethylcyclohexyl)-6-dimethylamino-s-triazine-2,4-(1H,3H)-dione, $n_D^{25}$ 1.5288

1-Methyl-3-(2,6-dimethylcyclohexyl)-6-dimethylamino-s-triazine-2,4-(1H,3H)-dione, $n_D^{25}$ 1.5244

1-Methyl-3-(2,3-dimethylcyclohexyl)-6-dimethylamino-s-triazine-2,4(1H,3H)-dione, $n_D^{25}$ 1.5283

1-Methyl-3-(4-methoxycylohexyl)-6-dimethylamino-s-triazine-2,4(1H,3H)-dione, $n_D^{25}$ 1.5305

1-Methyl-3-(4-ethoxycyclohexyl)-6-dimethylamino-s-triazine-2,4(1H,3H)-dione

1-Methyl-3-cycloheptyl-6-dimethylamino-s-triazine-2,4(1H,3H)-dione, m.p. 116°–118°

1-Methyl-3-cyclooctyl-6-dimethylamino-s-triazine-2,4(1H,3H)-dione, m.p. 133°–133.5°

1-Methyl-3-(3-chlorocyclobutyl)-6-dimethylamino-s-triazine-2,4(1H,3H)-dione, m.p. 160°

1-Methyl-3-(2-chlorocyclohexyl)-6-dimethylamino-s-triazine-2,4(1H,3H)-dione

1-Methyl-3-(4-chlorocyclohexyl)-6-dimethylamino-s-triazine-2,4(1H,3H)-dione

1-Methyl-3-(2-bromocyclohexyl)-6-dimethylamino-s-triazine-2,4(1H,3H)-dione

1-Methyl-3-(3,4-dichlorocyclohexyl)-6-dimethylamino-s-triazine-2,4(1H,3H)-dione

1-Methyl-3-(2,3-dichlorocyclopentyl)-6-dimethylamino-s-triazine-2,4(1H,3H)-dione 1-Methyl-3-(2,3,4,6-tetramethylcyclohexyl)-6-dimethylamino-s-triazine-2,4(1H,3H)-dione 1-Methyl-3-(3,3,5,5-tetramethylcyclohexyl)-6-dimethylamino-s-triazine-2,4(1H,3H)-dione 1-Methyl-3-(4-isopropylcyclohexyl)-6-dimethylamino-s-tri-azine-2,4(1H,3H)-dione, m.p. 128°–130°

1-Methyl-3-(2-decahydronaphthyl)-6-dimethylamino-s-tri-azine-2,4(1H,3H)-dione

1-Ethyl-3-isopropyl-6-dimethylamino-s-triazine-2,4(1H,3H)-dione, m.p. 63°–65°

1-Propyl-3-isopropyl-6-dimethylamino-s-triazine-2,4(1H,3H)-dione, $n_D^{25}$ 1.5056

1-Ethyl-3-cyclohexyl-6-dimethylamino-s-triazine-2,4(1H,3H)-dione, $n_D^{25}$ 1.5279

1-Methyl-3-(1-ethylcyclohexyl)-6-dimethylamino-s-triazine-2,4(1H,3H)-dione

1-Methyl-3-(1-butylcyclohexyl)-6-dimethylamino-s-triazine-2,4(1H,3H)-dione

1-Methyl-3-(2,4,6-trimethylcyclohexyl)-6-dimethylamino-s-triazine-2,4(1H,3H)-dione 1-Methyl-3-(1-decahydronaphthyl)-6-dimethylamino-s-triazine-2,4(1H,3H)-dione, m.p. 208°–211°

1-Methyl-3-n-propyl-6-methylamino-s-triazine-2,4(1H,3H)-dione, m.p. 189°–191°

1-Methyl-3-n-butyl-6-methylamino-s-triazine-2,4(1H,3H)-dione, m.p. 167°–168°

1-Methyl-3-n-hexyl-6-methylamino-s-triazine-2,4(1H,3H)-dione, $n_D^{25}$ 1.5130

1-Methyl-3-cyclohexyl-6-methylamino-s-triazine-2,4(1H,3H)-dione, m.p. 266.5°–268°

1-Methyl-3-(2,6-dimethylcyclohexyl)-6-methylamino-s-triazine-2,4(1H,3H)-dione, m.p. 128°–130°

1-Methyl-3-(3-cyclohexen-1-yl)-6-methylamino-s-triazine-2,4-(1H,3H)-dione

1-Methyl-3-ethyl-6-methylamino-s-triazine-2,4(1H,3H)-dione, m.p. 206°–207°

1-Methyl-3-(sec-butyl)-6-methylamino-s-triazine-2,4(1H,3H)-dione, m.p. 199°–200°

1-Methyl-3-(tert-butyl)-6-methylamino-s-triazine-2,4(1H,3H)-dione, m.p. 235°–235.5°

1-Methyl-3-phenyl-6-methylamino-s-triazine-2,4(1H,3H)-dione, m.p. 293°–296°

1-Methyl-3-(p-chlorophenyl)-6-methylamino-s-triazine-2,4-(1H,3H)-dione, m.p. > 300°

1-Methyl-3-(3,4-dichlorophenyl)-6-methylamino-s-triazine-2,4(1H,3H)-dione, m.p. > 300°

1-Methyl-3-(o-chlorophenyl)-6-methylamino-s-triazine-2,4-(1H,3H)-dione, m.p. > 300°

1-Methyl-3-(o-fluorophenyl)-6-methylamino-s-triazine-2,4-(1H,3H)-dione, m.p. > 300°

1-Methyl-3-(m-nitrophenyl)-6-methylamino-s-triazine-2,4-(1H,3H)-dione, m.p. > 300°

1-Methyl-3-(m-trifluoromethylphenyl)-6-methylamino-s-triazine-2,4(1H,3H)-dione, m.p. 241°–243°

1-Methyl-3-isopropyl-6-methylamino-s-triazine-2,4(1H,3H)-dione, m.p. 223°–224°

1-Ethyl-3-isopropyl-6-methylamino-s-triazine-2,4(1H,3H)-dione, m.p. 240°–241°

1-Propyl-3-isopropyl-6-methylamino-s-triazine-2,4(1H,3H)-dione, m.p. 166°–167°

1-Propyl-3-(p-chlorophenyl)-6-methylamino-s-triazine-2,4-(1H,3H)-dione, m.p. 261°–263°

1-Methyl-3-cycloheptyl-6-methylamino-s-triazine-2,4(1H,3H)-dione, m.p. 273°–274°

1-Methyl-3-cyclopentyl-6-methylamino-s-triazine-2,4(1H,3H)-dione, m.p. 220°–221.5°

1-Methyl-3-cyclooctyl-6-methylamino-s-triazine-2,4(1H,3H)-dione, m.p. > 300°

1-Methyl-3-(2-methylcyclohexyl)-6-methylamino-s-triazine-2,4(1H,3H)-dione, m.p. 246°–248.5°

1-Methyl-3-neopentyl-6-methylamino-s-triazine-2,4(1H,3H)-dione, m.p. 253°–255°

1-Ethyl-3-cyclohexyl-6-methylamino-s-triazine-2,4(1H,3H)-dione, m.p. 226°–227°

1-Methyl-3-(3-methylcyclohexyl)-6-methylamino-s-triazine-2,4(1H,3H)-dione, m.p. 255°–258°

1-Methyl-3-(m-tolyl)-6-methylamino-s-triazine-2,4(1H,3H)-dione, m.p. 280°–282°

1-Methyl-3-(3-chloro-p-tolyl)-6-methylamino-s-triazine-2,4(1H,3H)-dione, m.p. 321.5°–322.5°

1-Methyl-3-(2-methyl-5-chlorophenyl)-6-methylamino-s-triazine-2,4(1H,3H)-dione, m.p. 268°–270°

1-Methyl-3-(2,6-dimethylphenyl)-6-methylamino-s-triazine-2,4(1H,3H)-dione, m.p. 279.5°–282°
1-Methyl-3-(3-pentyl)-6-methylamino-s-triazine-2,4(1H,3H)-dione, m.p. 179°–182°
1-Methyl-3-(3,4-dimethylcyclohexyl)-6-methylamino-s-triazine-2,4(1H,3H)-dione, m.p. 295°–298°
1-Methyl-3-(p-isopropylphenyl)-6-methylamino-s-triazine-2,4(1H,3H)-dione, m.p. 284°–286°
1-Methyl-3-(2,3-dimethylcyclohexyl)-6-methylamino-s-triazine-2,4(1H,3H)-dione, m.p. 223°–225°
1-Methyl-3-(2,4-dimethylcyclohexyl)-6-methylamino-s-triazine-2,4(1H,3H)-dione, m.p. 214°–216°
1-Methyl-3-(4-isopropylcyclohexyl)-6-methylamino-s-triazine-2,4(1H,3H)-dione, m.p. 298°–300°
1-Methyl-3-(3,5-dimethylcyclohexyl)-6-methylamino-s-triazine-2,4(1H,3H)-dione, m.p. 250°–252°
1-Methyl-3-(1-methylcyclopentyl)-6-methylamino-s-triazine-2,4(1H,3H)-dione, m.p. 236°–238°
1-Methyl-3-(3-chlorocyclobutyl)-6-methylamino-s-triazine-2,4(1H,3H)-dione, m.p. 235°–236°
1-Methyl-3-octyl-6-methylamino-s-triazine-2,4(1H,3H)-dione, m.p. 89°–91°
1-Methyl-3-(p-methylthiophenyl)-6-methylamino-s-triazine-2,4(1H,3H)-dione, m.p. 314°–317°
1-Methyl-3-(2-methyl-4-chlorophenyl)-6-methylamino-s-triazine-2,4(1H,3H)-dione, m.p. 293°–295°
1-Methyl-3-(p-tolyl)-6-methylamino-s-triazine-2,4(1H,3H)-dione, m.p. 237°–240°
1-Methyl-3-isobutyl-6-methylamino-s-triazine-2,4(1H,3H)-dione, m.p. 206°–209°
1-Methyl-3-(1-decahydronaphthyl)-6-methylamino-s-triazine-2,4(1H,3H)-dione
1-Methyl-3-(2-cyclopentenyl)-6-methylamino-s-triazine-2,4(1H,3H)-dione
1-Methyl-3-(2-cyclooctenyl)-6-methylamino-s-triazine-2,4(1H,3H)-dione
1-Methyl-3-cyclopropylmethyl-6-methylamino-s-triazine-2,4-(1H,3H)-dione
1-Methyl-3-(3-methyl-4-methoxyphenyl)-6-methylamino-s-triazine-2,4(1H,3H)-dione
1-Methyl-3-(3-methyl-4-butoxyphenyl)-6-methylamino-s-triazine-2,4(1H,3H)-dione
1-Methyl-3-(2-methyl-4-methylthiophenyl)-6-methylamino-s-triazine-2,4(1H,3H)-dione
1-Methyl-3-(2,4-xylyl)-6-methylamino-s-triazine-2,4(1H,3H)-dione
1-Methyl-3-cyclohexyl-6-ethylamino-s-triazine-2,4(1H,3H)-dione, m.p. 209°–211°
1-Methyl-3-cyclohexyl-6-isopropylamino-s-triazine-2,4(1H,3H)-dione, m.p. 213°–215°
1-Methyl-3-ethyl-6-(tert-butylamino)-s-triazine-2,4(1H,3H)-dione, m.p. 182°–183.5°
1-Methyl-3-isopropyl-6-isopropylamino-s-triazine-2,4(1H,3H)-dione, m.p. 181°–184°
1-Methyl-3-isopropyl-6-propylamino-s-triazine-2,4(1H,3H)-dione
1-Methyl-3-isopropyl-6-(tert-butylamino)-s-triazine-2,4-(1H,3H)-dione, m.p. 185°–186.5°
1-Methyl-3-isopropyl-6-allylamino-s-triazine-2,4(1H,3H)-dione, m.p. 143.5°–145°
1-Methyl-3-isopropyl-6-propargylamino-s-triazine-2,4(1H,3H)-dione, $n_D^{25}$ 1.5520
1-Ethyl-3-(2-methylthiobutyl)-6-allylamino-s-triazine-2,4-(1H,3H)-dione
1-Ethyl-3-isopropyl-6-ethylamino-s-triazine-2,4(1H,3H)-dione, m.p. 170°–173°
1-Methyl-3-isopropyl-6-diethylamino-s-triazine-2,4(1H,3H)-dione, $n_D^{25}$ 1.5129
1-Methyl-3-isopropyl-6-(N-butyl-N-methylamino)-s-triazine-2,4(1H,3H)-dione, $n_D^{25}$ 1.5182
1-Methyl-3-cyclohexyl-6-(N-methyl-N-propylamino)-s-triazine-2,4(1H,3H)-dione, $n_D^{25}$ 1.5335
1-Methyl-3-cyclohexyl-6-(N,O-dimethylhydroxyamino)-s-tri-azine, 2,4(1H,3H)-dione
1-Methyl-3-cyclopentyl-6-(N,O-dimethylhydroxyamino)-s-triazine-2,4(1H,3H)-dione
1-Methyl-3-(2-norbornyl)-6-(N-methyl-N-ethylamino)-s-triazine-2,4(1H,3H)-dione
1-Methyl-3-(2-methoxyethyl)-6-(N-butyl-N-ethylamino)-s-triazine-2,4(1H,3H)-dione
1-Methyl-3-(2-ethoxybutyl)-6-(N-butyl-N-methylamino)-s-triazine-2,4-(1H,3H)-dione
1-Methyl-3-(2-ethylthiopropyl)-6-(N-butyl-N-methylamino)-s-triazine-2,4(1H,3H)-dione
1-Ethyl-3-cyclohexyl-6-[N-methyl-N-(2-butenyl)amino]-s-triazine-2,4(1H,3H)-dione
1-Ethyl-3-(2-chlorocyclohexyl)-6-(N-methyl-N-ethylamino)-s-triazine-2,4(1H,3H)-dione
1-Methyl-3-cyclohexyl-6-[N-methyl-N-(2-butynyl)amino]-s-triazine-2,4(1H,3H)-dione
1-Ethyl-3-(2-bromocyclohexyl)-6-(N-methyl-N-ethylamino)-s-triazine-2,4(1H,3H)-dione An alternate method for making those compounds of this invention where X is sulfur is illustrated by Equation 13:

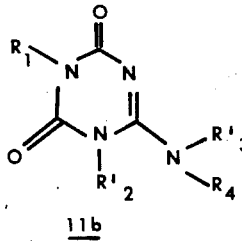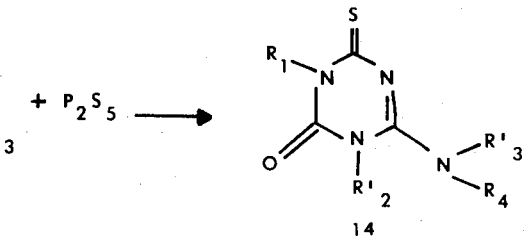

(compound 11 wherein $R_3$ is alkyl)

wherein
$R_1$, $R'_2$, $R'_3$ and $R_4$ are as previously defined.

The s-triazine-4-thio-2,4(1H,3H)-diones 14 can be prepared by heating corresponding oxygen analogs 11b with phosphorus pentasulfide at about 25° to 150° for about 1 to 12 hours in a solvent such as pyridine or picoline. The product can be isolated by dilution of the reaction mixture with a suitable hydrocarbon solvent (such as toluene), separating the solids (e.g. by filtration), and further extraction of the solids with the hydrocarbon solvent, followed by crystallization of the product from the hydrocarbon solvent extracts; or the reaction mixture can be treated with water, and the product extracted and crystallized as above.

The following example and Table IX illustrate this

Example 6

Synthesis of 1-Methyl-3-cyclohexyl-6-dimethylamino-s-triazine-4-thio-2,4(1H,3H)-dione To 25 parts of 1-methyl-3-cyclohexyl-6-dimethylamino-s-triazine-2,4-(1H,3H)-dione in 200 parts of pyridine is added 45 parts of phosphorus pentasulfide. The mixture is refluxed for six hours under a nitrogen atmosphere. The hot reaction mixture is diluted with 250 parts of toluene and the supernatent liquid decanted. The residue is mixed twice with 250-part portions of hot toluene and the supernatent liquid decanted. The combined supernatent liquid is concentrated to dryness and extracted with hot toluene. The hot extract is filtered, then cooled to give 18 parts of 1-methyl-3-cyclohexyl-6-dimethylamino-s-triazine-4-thio-2,4(1H,3H)-dione, m.p. 210°–212°.

TABLE X

Similarly the following 4-thio-s-triazinediones can be prepared.

1-Methyl-3-cyclopentyl-6-dimethylamino-s-triazine-4-thio-2,4(1H,3H)-dione; m.p. 184.5°–186°
1-Methyl-3-cyclooctyl-6-dimethylamino-s-triazine-4-thio-2,4(1H,3H)-dione
1-Ethyl-3-cyclohexyl-6-dimethylamino-s-triazine-4-thio-2,4(1H,3H)-dione
1-Propyl-3-cyclohexyl-6-dimethylamino-s-triazine-4-thio-2,4-(1H,3H)-dione
1-Methyl-3-phenyl-6-dimethylamino-s-triazine-4-thio-2,4(1H,3H)-dione
1-Methyl-3-norbornyl-6-dimethylamino-s-triazine-4-thio-2,4(1H,3H)-dione
1-Methyl-3-cyclohexylmethyl-6-dimethylamino-s-triazine-4-thio-2,4(1H,3H)-dione
1-Methyl-3-(2-norbornylmethyl)-6-dimethylamino-s-triazine-4-thio-2,4(1H,3H)-dione
1-Isopropyl-3-cyclohexyl-6-dimethylamino-s-triazine-4-thio-2,4(1H,3H)-dione
1-Methyl-3-cyclohexyl-6-(N-methyl-N-butyl)-6-dimethylamino-s-triazine-4-thio-2,4(1H,3H)-dione

Formulations and Use of the Compounds

The compounds of formula I are useful for control of undesired vegetation. They can be used wherever general weed control is required, such as industrial areas, railroad rights-of-way and areas adjacent to croplands in agricultural areas.

The precise amount of 6-aminotriazinedione to be used in any given situation will vary according to the particular end result desired, the use involved, the plant and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about ½ kilogram per hectare to about 25 kilograms per hectare.

The compounds of formula I may be combined with other herbicides and are particularly useful in combination with bromacil [3-(sec-butyl)-5-bromo-6-methyluracil], diuron [3-(3,4-dichlorophenyl)-1,1-dimethylurea], paraquat (1,1'-dimethyl-4,4'-bipyridinium ion), m-(3,3-dimethylureido)phenyl tert-butylcarbamate, 4-amino-6-tert-butyl-3-methylthio-as-triazin-5(4H)-one, and the s-triazines such as 2-chloro-4-ethylamino-6-isopropylamino-s-triazine, for controlling a broad spectrum of weeds.

The compounds of formula I can be formulated in the various ways which are conventional for herbicides of similar physical properties. Useful formulations include wettable and soluble powders, suspensions and solutions in solvents and oils, aqueous dispersions, dusts, granules, pellets, and high strength compositions. Broadly speaking, these formulations consist essentially of about 1 to 99% by weight of herbicidally active material (including at least one compound of formula I in a herbicidally effective amount) and at least one of a) about 0.1 to 20% by weight of surface active agent and b) about 5 to 99% by weight of solid or liquid diluent. More specifically, the various types of formulations will generally contain these ingredients in the following approximate proportions.

|  | Percent by Weight | | |
| --- | --- | --- | --- |
|  | Herbicide | Diluent | Surfactant |
| Wettable Powders | 25–90 | 0–74 | 1–10 |
| Suspensions or Solutions | 5–50 | 40–95 | 0–10 |
| Aqueous Dispersions | 10–50 | 40–89 | 1–10 |
| Dusts | 1–25 | 70–99 | 0–5 |
| Granules and Pellets | 1–35 | 65–99 | 0–15 |
| High-Strength Compositions | 90–99 | 0–10 | 0–2 |

The actual percentages that can be realized with a particular compound of formula I will depend upon its physical properties.

The manner of making and using such herbicidal formulations is described in numerous patents. See, for example, Luckenbaugh U.S. Pat. No. 3,309,192, Loux U.S. Pat. No. 3,235,357, Todd U.S. Pat. No. 2,655,445, Hamm et al. U.S. Pat. No. 2,863,752, Scherer et al. U.S. Pat. No. 3,079,244, Gysin et al. U.S. Pat. No. 2,891,855, and Barrous U.S. Pat. No. 2,642,354.

Many of the compounds of this invention possess unusually high water-solubility, up to several percent. This offers an advantage in, for instance, control of brush and other deep-rooted, perennial weeeds. An example of a highly water-soluble compound of this invention is 1-methyl-3-cyclohexyl-6-dimethylamino-s-triazine-2,4(1H,3H)-dione; this compound exhibits a solubility in water of about 3.2% at 25°C.

EXAMPLE 7

| Solution | |
| --- | --- |
| 1-Methyl-3-cyclohexyl-6-dimethylamino-s-triazine-2,4(1H,3H)-dione | 37% |
| Ethylene glycol monobutyl ether | 35 |
| Methanol | 9 |
| Water | 19 |

The ingredients are combined and stirred to produce a solution which can be extended with water for spraying.

EXAMPLE 8

| Wettable Powder | |
| --- | --- |
| 1-Methyl-3-cyclopentyl-6-dimethylamino-s-triazine-2,4(1H,3H)-dione | 25% |
| Diatomaceous earth | 71.5 |
| Dioctyl sodium sulfosuccinate | 1.5 |

-continued

| Wettable Powder | |
|---|---|
| Low-viscosity methyl cellulose | 2 | qualitative rating (type of injury) was also made; the letter "C" indicates chlorosis, and the letter "G" indicates growth retardation. Ratings in this test for some preferred compounds of the invention follow:

| Compound | Kg. Per Hr. | Postemergence | | | | Preemergence | | | |
|---|---|---|---|---|---|---|---|---|---|
| | | Nut-sedge | Johnson-grass | Crab-grass | Barnyard-grass | Crab-grass | Barnyard-grass | Sor-ghum | Wild Oats |
| 1-methyl-3-isopropyl-6-dimethylamino-s-triazine-2,4(1H,3H)-dione | 2.2 | 6C | 10C | 10C | 10C | 10C | 10C | 10C | 10C |
| | 0.44 | | | | | 10C | 10C | 10C | 10C |
| 3-isopropyl-6-dimethylamino-s-triazine-2,4(1H,3H)-dione | 2.2 | 0 | 10C | 10C | 10C | 10C | 10C | 10C | 10C |
| | 0.44 | | | | | 10C | 10C | 7C | 10C |
| 1-methyl-3-isopropyl-6-methylamino-s-triazine-2,4(1H,3H)-dione | 2.2 | 3G | 7C | 10C | 10C | 10C | 10C | 9C | 10C |
| | 0.44 | | | | | 9C | 10C | 7C | 9C |
| 1-methyl-3-sec-butyl-6-dimethylamino-s-triazine-2,4(1H,3H)-dione | 2.2 | 7C | 10C | 10C | 10C | 10C | 10C | 10C | 10C |
| | 0.44 | | | | | 9C | 10C | 9C | 10C |
| 1-methyl-3-cyclohexyl-6-dimethylamino-s-triazine-2,4(1H,3H)-dione | 2.2 | 8C | 10C | 10C | 10C | 9C | 10C | 10C | 10C |
| | 0.44 | | | | | 10C | 10C | 10C | 10C |
| 1-methyl-3-(3-chlorophenyl)-6-dimethyl-amino-s-triazine-2,4(1H,3H)-dione | 2.2 | 9C | 10C | 10C | 10C | 10C | 10C | 10C | 10C |
| | 0.44 | | | | | 10C | 10C | 9C | 10C |
| 1-methyl-3-cyclopentyl-6-dimethylamino-s-triazine-2,4(1H,3H)-dione | 2.2 | 9C | 10C | 10C | 10C | 10C | 10C | 10C | 10C |
| | 0.44 | | | | | 10C | 10C | 10C | 10C |
| 1-methyl-3-(2-methylcyclohexyl)-6-di-methylamino-s-triazine-2,4(1H,3H)-dione | 2.2 | 9C | 10C | 10C | 10C | 10C | 10C | 10C | 10C |
| | 0.44 | | | | | 10C | 10C | 10C | 10C |
| 1-methyl-3-(3-methylcyclohexyl)-6-di-methylamino-s-triazine-2,4(1H,3H)-dione | 2.2 | 10C | 10C | 10C | 10C | 10C | 10C | 10C | 10C |
| | 0.44 | | | | | 10C | 10C | 10C | 10C |
| 1-methyl-3-cyclohexyl-4-thio-6-di-methylamino-s-triazine-2,4(1H,3H)-dione | 2.2 | 10C | 10C | 10C | 10C | 9C | 10C | 9C | 10C |
| | 0.44 | | | | | 9C | 10C | 9C | 10C |

| Compound | Kg. Per Hr. | Preemergence | | | | | | |
|---|---|---|---|---|---|---|---|---|
| | | Nut-sedge | Cassia | Morning-glory | Mustard | Radish | Mari-gold | Dock |
| 1-methyl-3-isopropyl-6-dimethylamino-s-triazine-2,4(1H,3H)-dione | 2.2 | 2C | 10C | 10C | 10C | 10C | 10C | 10C |
| | 0.44 | 1C | 10C | 10C | 10C | 10C | 10C | 10C |
| 3-isopropyl-6-dimethylamino-s-triazine-2,4(1H,3H)-dione | 2.2 | 2C | 10C | 10C | 10C | 10C | 10C | 10C |
| | 0.44 | 0 | 10C | 10C | 10C | 10C | 10C | 10C |
| 1-methyl-3-isopropyl-6-methylamino-s-triazine-2,4(1H,3H)-dione | 2.2 | 0 | 10C | 10C | 10C | 10C | 10C | 9C |
| | 0.44 | 0 | 10C | 10C | 10C | 10C | 10C | 9C |
| 1-methyl-3-sec-butyl-6-dimethylamino-s-triazine-2,4(1H,3H)-dione | 2.2 | 6C | 10C | 10C | 10C | 10C | 10C | 10C |
| | 0.44 | 2C | 10C | 10C | 10C | 10C | 10C | 10C |
| 1-methyl-3-cyclohexyl-6-dimethylamino-s-triazine-2,4(1H,3H)-dione | 2.2 | 6C | 10C | 10C | 10C | 10C | 10C | 10C |
| | 0.44 | 2C | 10C | 10C | 10C | 10C | 10C | 10C |
| 1-methyl-3-(3-chlorophenyl)-6-dimethyl-amino-s-triazine-2,4(1H,3H)-dione | 2.2 | 6C | 10C | 10C | 10C | 10C | 10C | 10C |
| | 0.44 | 1C | 10C | 10C | 10C | 10C | 10C | 10C |
| 1-methyl-3-cyclopentyl-6-dimethylamino-s-triazine-2,4(1H,3H)-dione | 2.2 | 8C | 10C | 10C | 10C | 10C | 10C | 10C |
| | 0.44 | 7C | 10C | 10C | 10C | 10C | 10C | 10C |
| 1-methyl-3-(2-methylcyclohexyl)-6-di-methylamino-s-triazine-2,4(1H,3H)-dione | 2.2 | 5C | 10C | 10C | 10C | 10C | 10C | 10C |
| | 0.44 | 9C | 10C | 10C | 10C | 10C | 10C | 10C |
| 1-methyl-3-(3-methylcyclohexyl)-6-di-metylamino-s-triazine-2,4(1H,3H)-dione | 2.2 | 6C | 10C | 10C | 10C | 10C | 10C | 10C |
| | 0.44 | 8C | 10C | 10C | 10C | 10C | 10C | 10C |
| 1-methyl-3-cyclohexyl-4-thio-6-di-methylamino-s-triazine-2,4(1H,3H)-dione | 2.2 | 2C | 10C | 10C | 10C | 10C | 10C | 10C |
| | 0.44 | | 10C | 10C | 10C | 10C | 10C | 10C |

The ingredients are thoroughly blended and passed through a hammer mill to produce particles mostly all below 100 microns.

Herbicidal activity of compounds of this invention was discovered in a greenhouse test. In this test seeds of crabgrass (*Digitaria spp.*), barnyardgrass (*Echinochloa crusgalli*), wild oats (*Avena fatua*), nutsedge (*Cyperus rotundus*) Cassia tora, morninggglory (*Ipomoea spp.*) mustard (*Brassica spp.*), radish (*Raphanus spp.*), marigold (*Tagetes spp.*), dock (*Rumex crispus*), and nutsedge tubers were planted in a growth medium and treated preemergence at two rates (2.2 and 0.44 kg. per ha.) with the chemicals dissolved in a non-phytotoxic solvent. At the same time johnsongrass (*Sorghum halespense*) having four leaves, crabgrass and barnyardgrass with three leaves and nutsedge (*Cyperus rotundus*) from tubers with two leaves were treated postemergence at 2.2 kg per ha. Treated plants and controls were maintained in the greenhouse for sixteen days, then all species were compared to controls and visually rated for responses to treatment. A quantitative rating was made on a scale of 0 to 10; a rating of 10 means complete kill, a rating of 0 means no injury. A

I claim:
1. A compound of the formula:

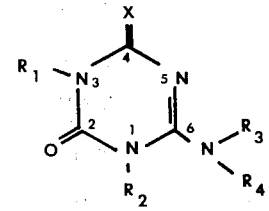

wherein
R₁ is selected from alkyl of 2 through 8 carbon atoms, alkenyl of 3 through 6 carbon atoms, alkynyl of 3 through through 6 carbon atoms, cycloalkyl of 4 through 8 carbon atoms, cycloalkenyl of 5 through 8 carbon atoms, cycloalkylmethyl of 4 through 9 carbon atoms, cycloalkenylmethyl of 6 through 9 carbon atoms, bicycloalkyl or bicycloalkenyl of 7 through 10 carbon atoms and bicycloalkylmethyl or bicycloalkenylmethyl of 8 through 11 carbon atoms, trimethylcyclohexyl and tetramethylcyclohexyl; the above alkyl groups substituted with one methoxy, ethoxy, methylthio or ethylthio group; the above cycloalkyl groups substituted with one alkyl of 2 through 4 carbon atoms, 1 through 2 methyl groups, 1 through 2 chlorines or bromines, one methoxy or one ethoxy group;
and

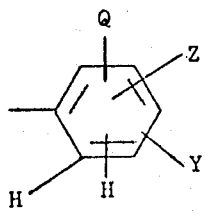

wherein
Q is hydrogen, fluorine, chlorine, bromine, alkyl of 1 through 4 carbon atoms, alkoxy or alkylthio of 1 through 2 carbon atoms, nitro or a trifluoromethyl group;
Y is hydrogen, chlorine, or methyl; and
Z is hydrogen or chlorine;
$R_2$ is hydrogen, alkyl of 1 through 3 carbon atoms or a cation selected from $Na^+$, $Li^+$, $K^+$, $(Ca/2)^+$, ammonium and dimethylammonium;
$R_3$ is hydrogen, methyl or ethyl;
$R_4$ is alkyl of 1 through 4 carbon atoms, alkenyl of 3 through 4 carbon atoms, alkynyl of 3 through 4 carbon atoms, or methoxy; and
X is oxygen or sulfur;
provided that when X is sulfur, neither $R_2$ nor $R_3$ is hydrogen.

2. A compound of claim 1 wherein:
$R_1$ is alkyl of 3 through 6 carbon atoms, cycloalkyl of 5 through 8 carbon atoms, or cycloalkyl of 5 through 8 carbon atoms substituted with one methyl group;
$R_2$, $R_3$ and $R_4$ are methyl; and
X is oxygen or sulfur.

3. A compound of claim 1 wherein:
$R_1$ is alkyl of 3 through 6 carbon atoms; cycloalkyl of 5 through 8 carbon atoms; cyclopentyl substituted with one methyl group; cyclohexyl substituted with 1 or 2 methyl groups; 3-trifluoromethylphenyl; cyclohexenyl; or decahydrophen-1-yl;
$R_2$ and $R_3$ are methyl;
$R_4$ is hydrogen; and
X is oxygen.

4. A compound of claim 1 wherein:
$R_1$ is cyclohexyl substituted with two methyl groups; 3-trifluoromethylphenyl; cyclohexenyl; decahydronaphthen-1-yl; or

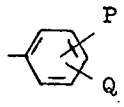

where
P is hydrogen, methyl, chlorine, or fluorine, and
Q is hydrogen or chlorine;
$R_2$, $R_3$, and $R_4$ are methyl; and
X is oxygen.

5. A compound of claim 3 wherein:
$R_1$ is alkyl of 3 through 4 carbon atoms; neopentyl; 1-ethylpropyl; n-hexyl; cycloalkyl of 5 through 8 carbon atoms; 2-methylcyclohexyl; 3-methylcyclohexyl; 2,3-dimethylcyclohexyl; 3,4-dimethylcyclohexyl; 2,4-dimethylcyclohexyl; 2,6-dimethylcyclohexyl; 3,5-dimethylcyclohexyl; 3-trifluoromethylphenyl; 3-cyclohexen-1-yl; or 1-decahydronaphthyl.

6. A compound of claim 4 wherein:
$R_1$ is 2,4-dimethylcyclohexyl; 2,6-dimethylcyclohexyl; 2,3-dimethylcyclohexyl; 3,4-dimethylcyclohexyl; 3-trifluoromethylphenyl; 3-cyclohexen-1-yl; 1-decahydronaphthyl; phenyl; 3-methyl phenyl; 4-methylphenyl; 3,4-dichlorophenyl; 2,5-dichlorophenyl; 2-chlorophenyl; 3-chlorophenyl; 4-chlorophenyl; 2-fluorophenyl; 3-fluorophenyl; 2-methyl-5-chlorophenyl; or 3-chloro-4-methylphenyl.

7. A compound of claim 1 wherein:
$R_1$ is cyclopentyl, methylcyclopentyl, cyclohexyl, or methylcyclohexyl;
$R_2$, $R_3$, and $R_4$ are methyl; and
X is oxygen.

8. Compound of claim 1:
1-Methyl-3-cyclohexyl-6-dimethylamino-s-triazine-2,4(1H,3H)-dione.

9. Compound of claim 1:
1-Methyl-3-cyclopentyl-6-dimethylamino-s-triazine-2,4(1H,3H)-dione.

10. A compound of claim 1 wherein $R_2$, $R_3$ and $R_4$ are all methyl.

11. A compound of claim 10 wherein $R_1$ is selected from:
alkyl of 2 through 8 carbon atoms,
alkenyl of 3 through 6 carbon atoms,
alkynyl of 3 through 6 carbon atoms,
cycloalkyl of 4 through 8 carbon atoms,
cycloalkenyl of 5 through 8 carbon atoms,
cycloalkylmethyl of 5 through 9 carbon atoms,
cycloalkenylmethyl of 6 through 9 carbon atoms,
bicycloalkyl of 7 through 10 carbon atoms,
bicycloalkenyl of 7 through 10 carbon atoms,
bicycloalkylmethyl of 8 carbon atoms,
bicycloalkenylmethyl of 8 through 11 carbon atoms,
trimethylcyclohexyl, and
tetramethylcyclohexyl; and
alkyl of 2 through 3 carbon atoms substituted with one methoxy, ethoxy, methylthio or ethylthio group,
cycloalkyl of 5 through 6 carbon atoms substituted with one methyl or two chloro groups,
cyclobutyl substituted with one chloro group, and
cyclohexyl substituted with one alkyl group of 2 through 4 carbon atoms, two methyl groups, one chloro group, one bromo group, one methoxy group or one ethoxy group; and

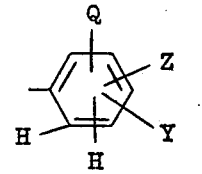

wherein
Q is hydrogen, fluorine, chlorine, bromine, alkyl of 1 through 4 carbon atoms, alkoxy or alkylthio of 1 through 2 carbon atoms, nitro or a trifluoromethyl group;
Y is hydrogen, chlorine, or methyl; and
Z is hydrogen or chlorine.

* * * * *